(12) United States Patent
Goto et al.

(10) Patent No.: US 7,696,129 B2
(45) Date of Patent: Apr. 13, 2010

(54) SUBSTITUTED AROMATIC AMIDE DERIVATIVE, INTERMEDIATE THEREOF, AGROHORTICULTURAL INSECTICIDE CONTAINING THEREOF AND METHOD FOR THE USE THEREOF

(75) Inventors: Makoto Goto, Yokohama (JP); Minoru Yamaguchi, Osakasayama (JP); Hiroto Harayama, Kawachinagano (JP); Hayami Nakao, Kawachinagano (JP); Takashi Furuya, Izumisano (JP); Masanori Tohnishi, Sakai (JP); Masayuki Morimoto, Kawachinagano (JP); Shinsuke Fujioka, Kawachinagano (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 1795 days.

(21) Appl. No.: 10/477,990

(22) PCT Filed: May 16, 2002

(86) PCT No.: PCT/JP02/04742

§ 371 (c)(1),
(2), (4) Date: Nov. 17, 2003

(87) PCT Pub. No.: WO02/094765

PCT Pub. Date: Nov. 28, 2002

(65) Prior Publication Data

US 2004/0152598 A1 Aug. 5, 2004

(30) Foreign Application Priority Data

May 18, 2001 (JP) ............................. 2001-149365

(51) Int. Cl.
*A61N 43/76* (2006.01)
*A01N 43/76* (2006.01)
*C07C 15/00* (2006.01)
*C07D 263/02* (2006.01)

(52) U.S. Cl. .................. 504/270; 514/374; 548/215; 585/24

(58) Field of Classification Search ................ 564/155; 514/617, 374; 548/215; 585/24; 504/270
See application file for complete search history.

(56) References Cited

U.S. PATENT DOCUMENTS 3,142,703 A 7/1964 Stecker

FOREIGN PATENT DOCUMENTS

| DE | 25 13 802 | | 10/1975 |
|----|-----------|---|---------|
| DE | 2513802 A1 | * | 10/1975 |
| EP | 0143302 A2 | * | 10/1984 |
| EP | 0143302 | | 6/1985 |
| EP | 919542 | | 6/1999 |
| EP | 919542 A2 | * | 6/1999 |
| EP | 0919542 A2 | * | 6/1999 |
| EP | 1006102 | | 6/2000 |
| EP | 1006107 | | 6/2000 |
| HU | 212435 | | 6/1996 |
| HU | 217361 | | 1/2000 |
| HU | P0004342 | | 4/2001 |
| HU | P0300263 | | 6/2003 |
| HU | P0300924 | | 8/2003 |
| JP | 61 289066 | | 12/1986 |
| JP | 61289066 | * | 12/1986 |
| WO | WO 02 096882 | | 12/2002 |

OTHER PUBLICATIONS

Database WPI, Derwent Pul., No. XP002231466, CA 1022573, Dec. 13, 1977.*
Database Crossfire Beilstein, No. xp 0022311482, J. Amer Chem Soc. vol. 94., 1972 pp. 820-828.*
Database WPI, Derwent Publications, No. XP002231466, CS 1022573, Dec. 13, 1977 Abstract.
Database Crossfire Beilstein, Beilstein Institut zur Foerderung der Chemischen Wissenschaften, No. xp0022311482, J. Amer. Chem Soc, vol. 94, 1972, pp. 820-828.

* cited by examiner

*Primary Examiner*—James O. Wilson
*Assistant Examiner*—Paul V. Ward
(74) *Attorney, Agent, or Firm*—Paul E. White, Jr.; Manelli Denison & Selter PLLC

(57) ABSTRACT

The present invention provides a substituted anilide derivative of formula (I):

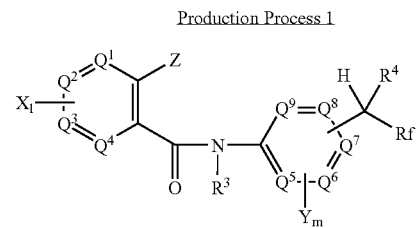

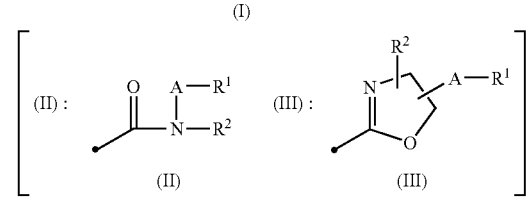

{wherein Z is a group of formula (II) or (III) (in these formulas, A is $C_1$-$C_6$ alkylene, $C_2$-$C_6$ alkenylene, etc., $R^1$ is H, halogen, —C($R^5$)=NO$R^6$, (substituted) phenyl, (substituted) heterocyclic ring, -$A^1$-$R^7$, etc.; $R^2$ is H, $C_1$-$C_4$ alkyl, etc.), $R^3$ is H, $C_1$-$C_4$ alkyl, etc.; $R^4$ is H, F, fluoro $C_1$-$C_6$ alkyl; Rf is F, fluoro $C_1$-$C_6$ alkyl; l is 0 to 2; Y is halogen, (substituted) phenyl, (substituted) phenoxy, etc.; and m is 0 to 3}, an intermediate thereof, an agrohorticultural agent, and a method for the use thereof. The compound of the present invention exhibits, at a low dosage, high uptake and translocation from the root and an excellent insecticidal effect especially when applied to soil.

13 Claims, No Drawings

SUBSTITUTED AROMATIC AMIDE DERIVATIVE, INTERMEDIATE THEREOF, AGROHORTICULTURAL INSECTICIDE CONTAINING THEREOF AND METHOD FOR THE USE THEREOF

This application is the national phase of international application PCT/JP02/04742 filed 16 May 2002 which designated the U.S.

TECHNICAL FIELD

The present invention relates to a substituted aromatic amide derivative, an intermediate thereof, an agrohorticultural insecticide containing said substituted aromatic amide derivative as an active ingredient, and a method for the use thereof.

BACKGROUND ART

Although JP-A-11-240857, JP-A-2001-131141, JP-A-2001-64258 and JP-A-2001-64268 disclose compounds which are considered analogous to the compound of the present invention, these patent gazettes neither disclose nor suggest the compounds which are represented by the general formula (I) of the present invention.

In the field of crop production such as agriculture, horticulture, etc., great injuries are done by pest insects even today, and development of a novel agrohorticultural insecticide is earnestly awaited, especially considering the appearance of resistant pest insecticides to the existing insecticides. At the same time, the age of agricultural workers becomes higher year by year, which makes it necessary to think out various labor-economizing methods of pesticide application and to create an agrohorticultural insecticide suitable for such new application methods.

DISCLOSURE OF THE INVENTION

The present inventors have conducted extensive studies with the aim of developing a novel agrohorticultural insecticide. As a result, it has been found that the fluoroalkyl-substituted aromatic amine derivatives represented by general formula (IV), which are new compounds not found in literature, are useful as an intermediate for the manufacture of various physiologically active derivatives such as medical drugs, pesticides, etc. Further, it has also been found that the substituted aromatic amide derivatives represented by general formula (I) derived from the above-mentioned compounds are new compounds not found in literature; and they exhibit an excellent insecticidal effect at a low dosage as compared with prior compounds found in literature, and exhibit high uptake and translocation from the root and an excellent insecticidal effect especially when applied to soil. Based on these findings, this invention has been accomplished.

Thus, the present invention relates to a substituted aromatic amide derivative represented by the following general formula (I):

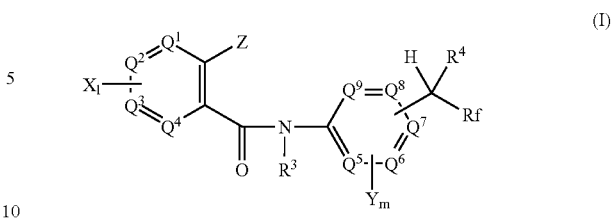

{wherein Z represents formula (II):

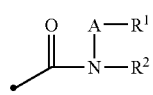

(wherein A, $R^1$ and $R^2$ are as defined below), or formula (III):

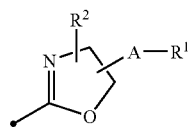

(wherein A represents a $C_1$-$C_6$ alkylene group; a substituted $C_1$-$C_6$ alkylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; a $C_2$-$C_6$ alkenylene group; a substituted $C_2$-$C_6$ alkenylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; a $C_2$-$C_6$ alkynylene group; or a substituted $C_3$-$C_6$ alkynylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; and an arbitrarily selected saturated carbon atom in the $C_1$-$C_6$ alkylene group, substituted $C_1$-$C_6$ alkylene group, $C_3$-$C_6$ alkenylene group, substituted $C_3$-$C_6$ alkenylene group, $C_3$-$C_6$ alkynylene group or substituted $C_3$-$C_6$ alkynylene group may be substituted with a $C_2$-$C_5$ alkylene group to form a $C_3$-$C_6$ cycloalkane ring, and arbitrarily selected two carbon atoms in the $C_2$-$C_6$ alkylene group, substituted $C_2$-$C_6$ alkylene group, $C_3$-$C_6$ alkenylene group or substituted $C_3$-$C_6$ alkenylene group may be taken conjointly together with an alkylene group or an alkenylene group to form a $C_3$-$C_6$ cycloalkane ring or a $C_3$-$C_6$ cycloalkene ring;

$R^1$ represents a hydrogen atom; a halogen atom; a cyano group; a nitro group; a $C_3$-$C_6$ cycloalkyl group; a $C_1$-$C_6$ alkoxycarbonyl group; a mono $C_1$-$C_6$ alkylaminocarbonyl group; a di $C_1$-$C_6$ alkylaminocarbonyl group which the $C_1$-$C_6$ alkyl groups may be the same or different; a mono $C_1$-$C_6$ alkylaminosulfonyl group; a di $C_1$-$C_6$ alkylaminosulfonyl group which the $C_1$-$C_6$ alkyl groups may be the same or different; a di $C_1$-$C_6$ alkoxyphosphoryl group which the $C_1$-$C_6$ alkyl groups may be the same or different; a di $C_1$-$C_6$ alkoxythiophosphoryl group which the $C_1$-$C_6$ alkyl groups may be the same or different; —C($R^5$)=N$OR^6$ (in this formula, $R^5$ represents a hydrogen atom or a $C_1$-$C_6$ alkyl group; and $R^6$ represents a hydrogen atom; a $C_1$-$C_6$ alkyl group; a $C_3$-$C_6$ alkenyl group; a $C_3$-$C_6$ alkynyl group; a $C_3$-$C_6$ cycloalkyl group; a phenyl $C_1$-$C_4$ alkyl group; or a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group and $C_1$-$C_6$ alkylthio group); a phenyl group; a substituted phenyl group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group; a substituted heterocyclic group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^1$-$R^7$ (in this formula, $A^1$ represents —O—, —S—, —SO—, —SO$_2$— or —N($R^6$)— (in this formula, $R^6$ is as defined above); and $R^7$ represents a hydrogen atom; a $C_1$-$C_6$ alkyl group; a halo $C_1$-$C_6$ alkyl group; a $C_3$-$C_6$ alkenyl group; a halo $C_3$-$C_6$ alkenyl group; a $C_3$-$C_6$ alkynyl group; a halo $C_3$-$C_6$ alkynyl group; a $C_3$-$C_6$ cycloalkyl group; a phenyl group; a substituted phenyl group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a phenyl $C_1$-$C_4$ alkyl group; a substituted phenyl $C_1$-$C_4$ alkyl group having, on the ring thereof, at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a heterocyclic group; a substituted heterocyclic group having, on the ring thereof, at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a $C_1$-$C_6$ alkylcarbonyl group; a halo $C_1$-$C_6$ alkylcarbonyl group; a $C_1$-$C_6$ alokoxycarbonyl group; a mono $C_1$-$C_6$ alkylaminocarbonyl group; a di $C_1$-$C_6$ alkylaminocarbonyl group which the $C_1$-$C_6$ alkyl groups may be the same or different; a $C_1$-$C_6$ alkylsulfonyl group; a halo $C_1$-$C_6$ alkylsulfonyl group; a mono $C_1$-$C_6$ alkylaminosulfonyl group; a di $C_1$-$C_6$ alkylaminosulfonyl group which the $C_1$-$C_6$ alkyl groups may be the same or different; a di $C_1$-$C_6$ alkoxyphosphoryl group which the $C_1$-$C_6$ alkyl groups may be the same or different; or a di $C_1$-$C_6$ alkoxythiophosphoryl group which the $C_1$-$C_6$ alkyl groups may be the same or different);

$R^2$ represents a hydrogen atom; a $C_1$-$C_4$ alkyl group; a $C_1$-$C_4$ alkoxy $C_1$-$C_4$ alkyl group; or a $C_1$-$C_4$ alkylthio $C_1$-$C_4$ alkyl group; and $R^2$ may be taken conjointly together with A or $R^1$ to form one to three, the same or different, 5- to 7-membered rings which may be intercepted by oxygen atom, sulfur atom or nitrogen atom);

$R^3$ represents a hydrogen atom; a $C_1$-$C_4$ alkyl group; a $C_1$-$C_4$ alkoxy $C_1$-$C_4$ alkyl group; or a $C_1$-$C_4$ alkylthio $C_1$-$C_4$ alkyl group;

$R^4$ represents a hydrogen atom; a fluorine atom; or a fluoro $C_1$-$C_6$ alkyl group; and Rf represents a fluorine atom; or a fluoro $C_1$-$C_6$ alkyl group;

$Q^1$ to $Q^9$, which may be the same or different, represent a carbon atom or a nitrogen atom;

X which may be the same or different represent a halogen atom; a nitro group; a cyano group; a $C_1$-$C_6$ alkyl group; a halo $C_1$-$C_6$ alkyl group; a $C_2$-$C_6$ alkenyl group; a halo $C_2$-$C_6$ alkenyl group; a $C_2$-$C_6$ alkynyl group; a halo $C_2$-$C_6$ alkynyl group; a $C_1$-$C_6$ alkoxy group; a halo $C_1$-$C_6$ alkoxy group; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; or a halo $C_1$-$C_6$ alkylsulfonyl group; and two groups of X residing in adjacent positions on the aromatic ring may be taken conjointly to form a fused ring, and said fused ring may have at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and 1 represents an integer of 0 to 2;

Y which may be the same or different represents a halogen atom; a $C_1$-$C_6$ alkyl group; a halo $C_1$-$C_6$ alkyl group; a cyclo $C_3$-$C_6$ alkyl group; a $C_1$-$C_6$ alkoxy group; a halo $C_1$-$C_6$ alkoxy group; a mono $C_1$-$C_6$ alkylamino group; a di $C_1$-$C_6$ alkylamino group which the $C_1$-$C_6$ alkyl groups may be the same or different, a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenyl $C_1$-$C_4$ alkyl group; a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenoxy group; a substituted phenoxy group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenylthio group; a substituted phenylthio group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group; or a substituted heterocyclic group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and two groups of Y residing in adjacent positions on the aromatic ring may be taken conjointly to form a fused ring, and said fused ring may have at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and Y may be taken conjointly together with $R^3$ to form a 5- to 7-membered ring which may be intercepted by one or two, the same or different oxygen atoms, sulfur atoms or nitrogen atoms; and m represents an integer of 0 to 3}, an agrohorticultural insecticide containing said compound as an active ingredient and a method for using the same.

The present invention further relates to a fluoroalkyl-substituted aromatic amine derivative represented by general formula (IV):

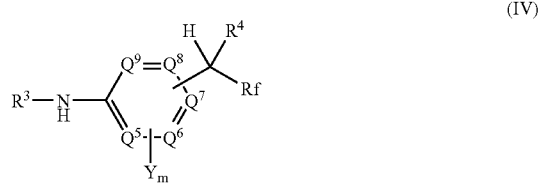

(IV)

(wherein $R^3$ represents a hydrogen atom; a $C_1$-$C_4$ alkyl group; a $C_1$-$C_4$ alkoxy $C_1$-$C_4$ alkyl group; or a $C_1$-$C_4$ alkylthio $C_1$-$C_4$ alkyl group; $R^4$ represents a hydrogen atom; a fluorine atom; or a fluoro $C_1$-$C_6$ alkyl group; and Rf represents a fluorine atom; or a fluoro $C_1$-$C_6$ alkyl group;

$Q^5$ to $Q^9$ which may be the same or different represent a carbon atom or a nitrogen atom;

Y which may be the same or different represents a halogen atom; a $C_1$-$C_6$ alkyl group; a halo $C_1$-$C_6$ alkyl group; a $C_1$-$C_6$ alkoxy group; a halo $C_1$-$C_6$ alkoxy group; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenyl $C_1$-$C_4$ alkyl group; a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenoxy group; or a substituted phenoxy group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and two groups of Y residing in the adjacent positions on the aromatic ring may be taken conjointly to form a fused ring, and said fused ring may have at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and m represents an integer of 0 to 3;

provided that when m represents an integer of 0, then $R^4$ is not a hydrogen atom or $R^4$ and Rf do not simultaneously represent a fluorine atom);

which is an intermediate compound for manufacture of the above-mentioned substituted aromatic amine derivative.

In the definition of general formula (I) representing the substituted aromatic amide derivatives of this invention, the term "halogen atom" means a chlorine atom, a bromine atom, an iodine atom or a fluorine atom; "n-" means normal, "s-" means secondary and "t-" means tertiary; "$C_1$-$C_6$ alkyl" means a straight or branched chain alkyl group having 1 to 6 carbon atoms such as methyl, ethyl, n-propyl, i-propyl, n-butyl, i-butyl, s-butyl, t-butyl, n-pentyl, neopentyl, n-hexyl and the like; "$C_1$-$C_6$ haloalkyl" means a straight or branched chain alkyl group having 1 to 6 carbon atoms which is substituted with at least one, the same or different halogen atoms, such as trifluoromethyl group, difluoromethyl group, perfluoroethyl group, perfluoroisopropyl group, chloromethyl group, bromomethyl group, 1-bromoethyl group, 2,3-dibromopropyl group and the like; "$C_1$-$C_6$ alkylene" means a straight or branched chain alkylene group having 1 to 6 carbon atoms such as methylene, ethylene, propylene, trimethylene, dimethylmethylene, tetramethylene, isobutylene, dimethylethylene, hexamethylene and the like; and "$C_2$-$C_6$ alkenylene" or "$C_2$-$C_6$ alkynylene" similarly means a straight or branched chain alkenylene or alkynylene group having 2 to 6 carbon atoms; "$C_3$-$C_6$ cycloalkyl" means an alicyclic alkyl group having 3-6 carbon atoms, such as cyclopropyl, cyclobutyl, cyclopentyl, cyclohexyl and the like.

As the "heterocyclic group", mention can be made of, for example, pyridyl group, pyridine-N-oxide group, pyrimidinyl group, furyl group, tetrahydrofuryl group, thienyl group, tetrahydrothienyl group, tetrahydropyranyl group, tetrahydrothiopyranyl group, oxazolyl group, isoxazolyl group, oxadiazolyl group, thiazolyl group, isothiazolyl group, thiadiazolyl group, imidazolyl group, triazolyl group, pyrazolyl group and the like. As the "fused ring", mention can be made of, for example, naphthalene, tetrahydronaphthalene, indene, indane, quinoline, quinazoline, indole, indoline, chroman, isochroman, benzodioxane, benzodioxole, benzofuran, dihydrobenzofuran, benzothiophene, dihydrobenzothiophene, benzoxazole, benzothiazole, benzimidazole, indazole, and the like.

In some cases, the substituted aromatic amide derivative represented by general formula (I) may have one or plural asymmetric carbon atoms or asymmetric centers in the structural formula thereof and may have two or more optical isomers and diastereomers. In such cases, the present invention involves all such optical isomers and mixtures of such optical isomers at any proportions. Further, in some cases, the substituted aromatic amide derivative represented by general formula (I) of the present invention may have two geometrical isomers due to carbon-carbon double bond or carbon-nitrogen double bond in the structural formula thereof. In such a case, the present invention involves all such geometrical isomers and mixtures of such geometrical isomers in any proportions.

In the substituted aromatic amide derivatives represented by general formula (I) of the present invention, A is preferably a $C_1$-$C_6$ alkylene group and further preferably a $C_3$-$C_6$ alkylene group; $R^1$ is preferably a hydrogen atom or a group -$A^1$-$R^7$ and further preferably $A^1$-$A^7$ in which $A^1$ is S, SO or $SO_2$ and $R^7$ is a $C_1$-$C_6$ alkyl group. $R^2$ is preferably a hydrogen atom or a $C_1$-$C_4$ alkyl group, and further preferably a hydrogen atom; $R^3$ is preferably a hydrogen atom or a $C_1$-$C_4$ alkyl group, and further preferably a hydrogen atom; $R^4$ is preferably a hydrogen atom or a fluoro $C_1$-$C_6$ alkyl group, and further preferably a fluoro $C_1$-$C_3$ alkyl group; Rf is preferably a fluoro $C_1$-$C_6$ alkyl group, and further preferably a $C_1$-$C_3$ alkyl group; $Q^1$ to $Q^9$ represent a carbon atom or a nitrogen atom, and further preferably $Q^1$ to $Q^5$ and $Q^7$ to $Q^9$ represent a carbon atom and $Q^6$ is a carbon atom or a nitrogen atom; X is preferably a halogen atom, and further preferably an iodine atom; l preferably represents 1; Y is preferably a halogen atom or a $C_1$-$C_6$ alkyl group, and further preferably a methyl group; and m preferably represents 1.

The substituted aromatic amide derivatives represented by general formula (I) and the fluoroalkyl-substituted aromatic amine derivatives represented by general formula (IV) can be produced from the fluoroalkyl-substituted aromatic amine derivatives represented by general formula (IV) which can be produced according to the process disclosed in, for instance, in JP-A-11-302233, European Patent No. 1006102, etc., according to the process scheme shown below, for example. It is also possible, however, to produce the substituted aromatic amide derivatives of general formula (I) according to the processes disclosed in JP-A-11-240857, JP-A-2001-131141, JP-A-2001-64258, JP-A-2001-64268, etc.

Production Process 1

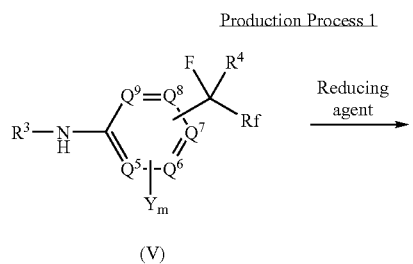

(V)

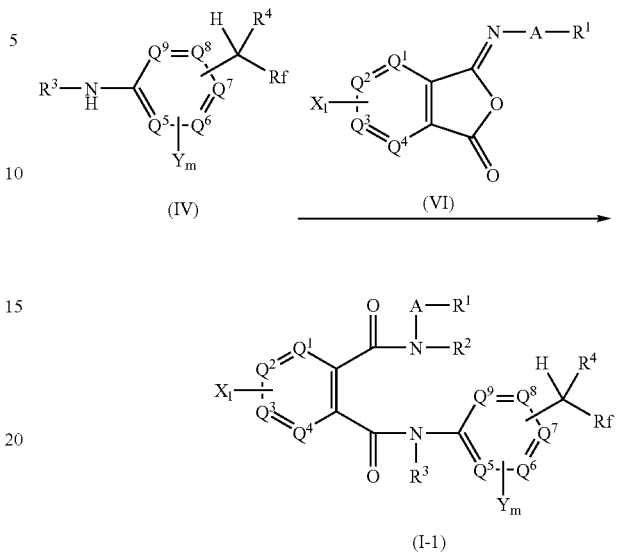

wherein $R^1$, $R^2$, $R^3$, $R^4$, Rf, Y, m, X, l, $Q^1$, $Q^2$, $Q^3$, $Q^4$, $Q^5$, $Q^6$, $Q^7$, $Q^8$ and $Q^9$ are as defined above.

A fluoroalkyl-substituted aromatic amine represented by general formula (V) is subjected to a reduction in the presence or absence of an inert solvent, in the presence of a reducing agent to form a fluoroalkyl-substituted aromatic amine derivative represented by general formula (IV). After isolating or not isolating said fluoroalkyl-substituted aromatic amine derivative, it is reacted with a phthalic acid isoimide represented by general formula (VI), whereby a substituted aromatic amide derivative represented by general formula (I-1) can be obtained.

1-1. General Formula (V)→General Formula (IV)

As the reducing agent used in this reaction, for example, metal hydrides such as lithium aluminum hydride, sodium bis(2-methoxyethoxy)aluminum hydride, sodium borohydride and the like, metals such as metallic lithium and the like, and metallic salts can be referred to, and the amount of the reducing agent may be appropriately selected from a range of from an equivalent amount to an excessive amount based on the fluoroalkyl-substituted aromatic amine represented by general formula (V).

The solvent used in this reaction may be any solvent so far as the solvent does not disturb the progress of this reaction markedly, and examples of such a solvent include aromatic hydrocarbons such as benzene, toluene, xylene and the like, halogenated hydrocarbons such as methylene chloride, chloroform, carbon tetrachloride and the like, halogenated aromatic hydrocarbons such as chlorobenzene, dichlorobenzene and the like, acyclic and cyclic ethers such as diethyl ether, dioxane, tetrahydrofuran and the like, etc. These inert solvents may be used either alone or in the form of a mixture of two or more.

The reaction can be carried out at a temperature ranging from room temperature to the boiling temperature of the used inert solvent. Although the reaction time varies depending on the scale and temperature of the reaction, it is in the range of from several minutes to 50 hours.

After completion of the reaction, the product is isolated from the reaction system containing the objective compound in the conventional method. The objective compound can be produced by purification such as recrystallization, column chromatography, etc., according to the need. It is also possible to feed the objective compound to the next step of the reaction, without isolation from the reaction system.

1-2. General Formula (IV)→General Formula (I-1)

The fluoroalkyl-substituted aromatic amine derivative of general formula (IV) is reacted with a phthalic acid isoimide represented by general formula (VI) in the presence of an inert solvent, whereby a substituted aromatic amide derivative represented by general formula (I-1) can be obtained.

This reaction may be carried out in the presence of an acid or a base, of which amount may be varied in the range from a catalytic amount to an excessive amount according to the need.

As the inert solvent used in this reaction, any solvent may be used so far as the solvent does not disturb the progress of the reaction markedly. Examples of the inert solvent include aromatic hydrocarbons such as benzene, toluene, xylene and the like; halogenated hydrocarbons such as methylene chloride, chloroform, carbon tetrachloride and the like; halogenated aromatic hydrocarbons such as chlorobenzene, dichlorobenzene and the like; acyclic and cyclic ethers such as diethyl ether, dioxane, tetrahydrofuran and the like; esters such as ethyl acetate and the like; nitriles such as acetonitrile and the like; amides such as dimethylformamide, dimethylacetamide and the like; acids such as acetic acid and the like; dimethyl sulfoxide; 1,3-dimethyl-2-imidazolidinone; etc. These inert solvents may be used either alone or in the form of a mixture of two or more.

Since this reaction is an equimolar reaction, the reactants may be used in equimolar amounts. It is also possible to use any one of the reactants in an excessive amount. If desired, the reaction may be carried out under a dehydrating condition.

The reaction can be carried out at a temperature ranging from room temperature to the boiling temperature of the used inert solvent.

Although the reaction time varies depending on the scale and temperature of the reaction, it is in the range of from several minutes to 48 hours.

After completion of the reaction, the product is isolated from the reaction system containing the objective compound in the conventional method. The objective compound can be produced by purification such as recrystallization, column chromatography, etc., according to the need.

In the case that $R^1$ represents $-A^1-R^7$ in the general formula (I-1), the compound wherein $A^1$ is —SO— or —SO$_2$— can be prepared from the compound wherein $A^1$ is —S— by the usual method, for example, an oxidation of the compound wherein $A^1$ is —S— with the oxidizing agent such as m-chloroperbenzoic acid.

The phthalic acid isoimide represented by general formula (VI) can be produced according to the method described in, for example, J. Med. Chem., 10, 982 (1967).

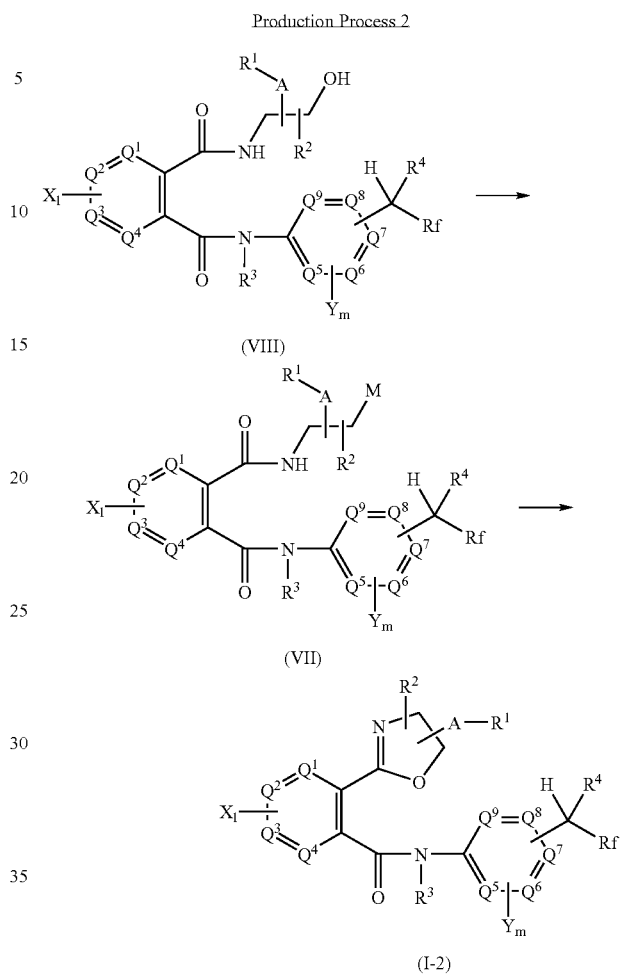

Production Process 2 wherein A, $R^1$, $R^2$, $R^3$, $R^4$, Rf, X, l, Y, m, $Q^1$, $Q^2$, $Q^3$, $Q^4$, $Q^5$, $Q^6$, $Q^7$, $Q^8$ and $Q^9$ are as defined above, and M represents a halogen atom or $R^8SO_3^-$ wherein $R^8$ represents a $C_1$-$C_6$ alkyl group such as methyl group or the like or a phenyl group which may have a substituent such as methyl group or the like on the para position thereof.

A diamide represented by general formula (VIII) is reacted with a halogenating agent or a sulfonic ester-forming agent in the presence or absence of an inert solvent to form a compound represented by general formula (VII), and then the compound (VII) is subjected to a cyclization reaction under a heating condition or by the use of a base or the like, whereby a substituted aromatic amide derivative represented by general formula (I-2) can be obtained.

2-1. General Formula (VIII)→General Formula (VII)

As the halogenating agents which can be used in this reaction, diethylamino sulfur trifluoride (DAST), thionyl chloride, phosphorus oxychloride, and combination of triphenylphosphine and carbon tetrabromide or carbon tetrachloride can be referred to. As the sulfonic acid-forming agents which can be used, sulfonic acid halides such as methaneuslfonyl chloride, p-toluenesulfonyl chloride and the like can be referred to. The amount of the halogenating agent or the sulfonic ester-forming agent may be appropriately selected from a range of from an equimolar amount to an excessive molar amount based on the diamide represented by general formula (VIII).

As the bases which can be used in this reaction, for example, organic bases such as triethylamine, pyridine and the like and inorganic bases such as potassium carbonate and the like can be referred to. The amount of said base may be appropriately selected from a range of from an equimolar amount to an excessive molar amount based on the diamide of general formula (VIII).

As the inert solvent, the same ones as mentioned in the paragraph of Production Process 1 can be used. Apart from them, other inert solvents such as pyridine and the like can also be used for this purpose.

The reaction can be carried out at a temperature ranging from −20° C. to the boiling point region of the used inert solvent. Although the reaction time may vary depending on the scale and temperature of the reaction, the reaction time is in the range of several minutes to 48 hours.

After completion of the reaction, the product is isolated from the reaction system containing the objective compound in the conventional method, and purified by recrystallization, column chromatography, etc. according to the need, whereby the objective compound can be obtained.

The diamides represented by general formula (VIII) can be produced according to Production Process 1.

2-2. General Formula (VII)→General Formula (I-2)

As the base and the inert solvent used in this reaction, for example, the same bases and inert solvents as mentioned in the paragraph of Production Process 2-1 can be used.

The amount of said base may be appropriately selected from a range of from an equimolar amount to an excessive amount based on the compound of general formula (VII).

The reaction can be carried out at a temperature ranging from −20° C. to the boiling point region of the used inert solvent. Although the reaction time may vary depending on the scale and temperature of the reaction, the reaction time is in the range of several minutes to 48 hours.

After completion of the reaction, the product is isolated from the reaction system containing the objective compound in the conventional method, and purified by recrystallization, column chromatography, etc. according to the need, whereby the objective compound can be obtained.

In the case that $R^1$ represents $-A^1-R^7$ in the general formula (I-1), the compound wherein $A^1$ is —SO— or —$SO_2$— can be prepared from the compound wherein $A^1$ is —S— by the usual method, for example, an oxidation of the compound wherein $A^1$ is —S— under the oxidizing agent such as m-chloroperbenzoic acid.

Next, typical examples of the fluoroalkyl-substituted aromatic amine derivative represented by general formula (IV) are listed in Tables 1 to 4, and typical examples of the substituted aromatic amide represented by general formula (I) are listed in Tables 5 to 10. This invention is by no means limited thereby.

In the tables, "Me" means methyl group, "Et" means ethyl group, "Pr" means propyl group, and "Ph" means phenyl group.

TABLE 1

General Formula (IV-I)

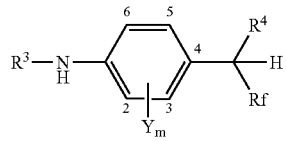

(IV-1)

| No. | $R^3$ | $R^4$ | Rf | $Y_m$ | NMR $^1$H-NMR[CDCl$_3$/TMS, δ (ppm)] |
|---|---|---|---|---|---|
| 1-1 | H | H | $CF_3$ | 2-F | 3.24 (q.2H), 3.7 (br.2H), 6.71-6.98 (m.3H). |
| 1-2 | H | H | $CF_3$ | 2-Cl | 3.23 (q.2H), 4.0 (br.2H), 6.74 (d.1H), 6.95 (d.1H), 7.20 (s.1H). |
| 1-3 | H | H | $CF_3$ | 2-Me | 2.16 (s.3H), 3.22 (q.2H), 3.6 (br.2H), 6.64 (d.1H), 6.95 (d.1H), 6.97 (s.1H). |
| 1-4 | H | H | $CF_3$ | 2-Et | 3.9 (br.2H), 6.68 (d.1H), 6.95-6.98 (m.2H). |
| 1-5 | H | H | $C_2F_5$ | 2-Me | 2.17 (s.3H), 3.19 (t.2H), 3.8 (br.2H), 6.67 (d.1H), 6.94-6.97 (d.1H). |
| 1-6 | H | H | $C_2F_5$ | 2-F | 3.33 (t.2H), 4.0 (br.2H), 6.8-7.0 (m.3H). |
| 1-7 | H | H | n-$C_3F_7$ | 2-Me | 2.18 (s.3H), 3.24 (t.2H), 3.6 (br.2H), 6.67 (d.1H), 6.90-6.99 (m.2H). |
| 1-8 | H | H | n-$C_5F_{11}$ | 2-$CH_2$-$C_5F_{11}$-n | 2.23 (s.3H), 3.28 (dt.4H), 3.8 (br.2H), 6.93 (s.1H), 7.01 (s.1H). |
| 1-9 | H | $CF_3$ | $CF_3$ | H | 3.93 (m.1H), 3.95 (br.2H), 6.72 (d.2H), 7.18 (d.2H). |
| 1-10 | H | $CF_3$ | $CF_3$ | 2-F | 3.91 (m.1H), 4.0 (br.2H), 6.8 (t.1H), 6.95 (d.1H), 7.85 (d.1H). |
| 1-11 | H | $CF_3$ | $CF_3$ | 2-Cl | 3.89 (m.1H), 4.06 (br.2H), 6.80 (d.1H), 7.10 (d.1H), 7.29 (s.1H). |
| 1-12 | H | $CF_3$ | $CF_3$ | 2-Me | 2.19 (s.3H), 3.89 (m.1H), 4.0 (br.2H), 6.71 (d.1H), 7.06 (m.2H). |
| 1-13 | H | $CF_3$ | $CF_3$ | 2-Et | 1.27 (t.3H), 2.52 (q.2H), 3.85 (m.1H), 3.9 (br.2H), 6.69 (d.1H). 7.06 (m.3H). |
| 1-14 | H | $CF_3$ | $CF_3$ | 2-Cl-6-Me | 2.12 (s.3H), 3.86 (m.1H), 4.02 (br. 2H), 6.78 (s. 1H), 7.19 (s.1H). 7.18 (s.1H). |

TABLE 1-continued

General Formula (IV-1)

(IV-1)

$R^3-NH$—(phenyl ring, positions 2,3,4,5,6 with $Y_m$)—$C(R^4)(H)(Rf)$

| No. | $R^3$ | $R^4$ | Rf | Ym | NMR $^1$H-NMR[CDCl$_3$/TMS, δ (ppm)] |
|---|---|---|---|---|---|
| 1-15 | H | CF$_3$ | CF$_3$ | 2,6-Cl$_2$ | 3.87 (m.1H), 4.65 (br.2H), 7.24 (s.1H). |
| 1-16 | H | CF$_3$ | CF$_3$ | 2-OMe | 3.75 (s.3H), 3.93 (m.1H), 4.1 (br.2H), 6.70 (d.1H), 7.08 (d.1H), 7.32 (s.1H), |
| 1-17 | H | CF$_3$ | CF$_3$ | 2-SMe | 2.71 (s.3H), 3.90 (m.1H), 4.25 (br.2H), 6.73 (d.1H), 7.12 (d.1H), 7.36 (s.1H). |
| 1-18 | H | CF$_3$ | CF$_3$ | 2-NO$_2$ | 4.10 (m.1H), 6,5 (br.2H), 6.82 (d.1H), 7.50 (d.1H), 8.11 (s.1H). |
| 1-19 | H | CF$_3$ | CF$_3$ | 2-OPh | 3.86 (m.1H), 4.6 (br.2H), 6.8-6.9 (m.2H), 6.9-7.0 (m.3H), 7.1 (t.1H), 7.34 (t.2H). |
| 1-20 | H | CF$_3$ | CF$_3$ | 2-Me-3-F | 2.11 (s.3H), 4.49 (m.1H), 4.5 (br.2H), 6.55 (d.1H), 7.19 (t.1H). |
| 1-21 | H | CF$_3$ | CF$_3$ | 2-Me-5-F | 2.16 (s.3H), 4.46 (m.1H), 4.5 (br.2H), 6.47 (d.1H), 7.16 (d.1H), 7.25 (s.1H). |
| 1-22 | H | CF$_3$ | CF$_3$ | 2-Me-3-Cl | 2.27 (s.3H), 4.3 (br.2H), 4.96 (m.1H), 6.65 (d.1H), 6.8 (d.1H). |
| 1-23 | H | CF$_3$ | CF$_3$ | 2-Me-3-OMe | 2.13 (s.3H), 3.83 (s.3H), 4.0 (br.1H), 4.48 (m.1H), 6.51 (d.1H), 7.28 (d.1H). |
| 1-24 | H | CF$_3$ | CF$_3$ | 2,6-Me$_2$ | 2.20 (s.6H), 3.83 (m.1H), 3.95 (br.2H), 6.97 (s.2H). |
| 1-25 | Me | CF$_3$ | CF$_3$ | 2-Me | 2.16 (s.3H), 2.91 (s.3H), 3.90 (m.1H), 3.95 (br.1H), 6.64 (d.1H), 7.06 (s.1H), 7.17 (d.1H). |
| 1-26 | i-Pr | CF$_3$ | CF$_3$ | 2-Me | 1.24 (d.6H), 2.11 (s.3H), 3.67 (m.1H), 3.87 (br.1H), 6.60 (d.1H), 7.04 (s.1H), 7.12 (d.1H). |
| 1-27 | H | CF$_3$ | C$_2$F$_5$ | 2-Me | 2.19 (s.3H), 3.85-4.00 (m.1H), 4.1 (br.2H), 6.70 (d.1H), 7.0-7.22 (m. 2H). |
| 1-28 | H | CF$_3$ | CF$_3$ | 2-Br | 3.90 (m.1H), 4.00 (br.2H), 6.77 (d.1H), 7.14 (s.1H), 7.44 (d.1H). |
| 1-29 | H | CF$_3$ | C$_2$F$_5$ | 2-I | 3.87 (m.1H), 4.30 (br.2H), 6.74 (d.1H), 7.19 (dd.1H), 7.65 (d.1H). |
| 1-30 | H | CF$_3$ | CF$_3$ | 2-CN | 3.93 (m,1H), 4.65 (br.2H), 6.79 (d.1H), 7.35 (dd.1H), 7.43 (d.1H). |

TABLE 2

General Formula (IV-2)

(IV-2)

| No. | $R^3$ | $R^4$ | Rf | Ym | NMR $^1$H-NMR[CDCl$_3$/TMS, δ (ppm)] |
|---|---|---|---|---|---|
| 2-1 | H | CF$_3$ | CF$_3$ | H | 3.9 (br.2H), 4,20 (m.1H), 6.58 (d.1H), 6.69 (s.1H), 6.80 (d.1H), 7.16 (t.1H) |
| 2-3 | H | CF$_3$ | CF$_3$ | 6-Cl | 4.1 (br.2H), 4.22 (m.1H), 6.67 (d.1H), 6.83 (s.1H), 7.15 (d.1H) |

TABLE 3

General Formula (IV-3)

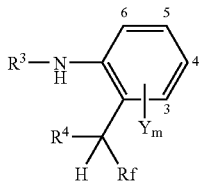

(IV-3)

| No. | R³ | R⁴ | Rf | Ym | NMR ¹H-NMR[CDCl₃/TMS, δ (ppm)] |
|---|---|---|---|---|---|
| 3-1 | H | CF₃ | CF₃ | 4-Me | 2.29 (s.3H), 4.2 (br.2H), 4.56 (m.1H), 6.80 (d.1H), 7.30 (d.1H), 7.24 (s.1H). |
| 3-2 | H | CF₃ | CF₃ | 4-OMe | 3.77 (s.3H), 3.8 (br.2H), 4.33 (m.1H), 6.85 (s.1H), 7.01 (d.1H), 7.25 (s.1H). |
| 3-3 | H | CF₃ | CF₃ | 4-SMe | 2.44 (s.3H), 4.2 (br.2H), 4.50 (m.1H), 6.83 (d.1H), 7.25 (d.1H), 7.40 (s.1H). |

TABLE 4

General Formula (IV-4)

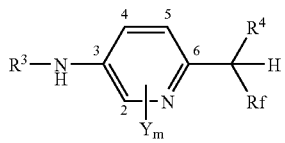

(IV-4)

| No. | R³ | R⁴ | Rf | Ym | NMR ¹H-NMR[CDCl₃/TMS, δ (ppm)] |
|---|---|---|---|---|---|
| 4-1 | H | CF₃ | CF₃ | H | 3.82 (br.2H), 4.30 (m.1H), 7.00 (dd.1H), 7.28 (d.1H), 8.07 (d.1H) |
| 4-2 | H | CF₃ | CF₃ | 2-Cl | 4.28 (m.1H), 4.30 (br.2H), 7.07 (d.1H), 7.27 (d.1H) |
| 4-3 | H | CF₃ | CF₃ | 2-Br | 4.30 (m.1H), 4.34 (br.2H), 7.07 (d.TH), 7.27 (d.1H) |
| 4-4 | H | CF₃ | CF₃ | 2-Me | 2.40 (s.3H), 3.76 (br.2H), 4.32 (m.1H), 6.95 (d.1H), 7.20 (d.1H) |
| 4-5 | H | CF₃ | CF₃ | 4-Me | 2.20 (s.3H), 3.80 (br.2H), 4.28 (m.1H), 7.17 (d.1H), 8.01 (d.1H) |
| 4-6 | H | CF₃ | CF₃ | 2-Me-6-Cl | 2.24(s.3H), 4.23 (br.2H), 4.26 (m.1H), 7.16 (s.1H) |
| 4-7 | H | CF₃ | CF₃ | 2,6-Br₂ | 4.31 (m.1H), 4.80 (br.2H), 7.53 (d.1H) |
| 4-8 | H | CF₃ | CF₃ | 2,6-Cl₂ | 4.28 (m.1H), 4.70 (br.1H), 7.39 (s.1H) |

TABLE 5

General Formula (I-3)
(Q¹ – Q⁶, Q⁸, Q⁹=C, R²=R³=H)

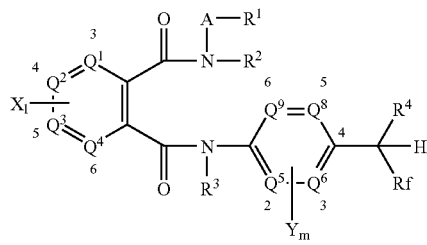

(I-3)

| No. | -A-R¹ | R⁴ | Rf | Xl | Ym | m.p. (° C.) |
|---|---|---|---|---|---|---|
| 5-1 | C(Me)₂CH₂SMe | H | CF₃ | 3-I | 2-Me | 173 |
| 5-2 | C(Me)₂CH₂SMe | H | CF₃ | 3-I | 2-Et | 153 |
| 5-3 | C(Me)₂CH₂SMe | H | CF₃ | 3-I | 2-F | 178 |

TABLE 5-continued

General Formula (I-3)
($Q^1$ – $Q^6$, $Q^8$, $Q^9$=C, $R^2$=$R^3$=H)

(I-3)

| No. | -A-$R^1$ | $R^4$ | Rf | Xl | Ym | m.p. (° C.) |
|---|---|---|---|---|---|---|
| 5-4 | C(Me)$_2$CH$_2$SMe | H | CF$_3$ | 3-I | 2-Cl | 126 |
| 5-5 | C(Me)$_2$CH$_2$SMe | H | C$_2$F$_5$ | 3-I | 2-Me | 196 |
| 5-6 | C(Me)$_2$CH$_2$SMe | H | C$_2$F$_5$ | 3-I | 2-F | 168 |
| 5-7 | C(Me)$_2$CH$_2$SMe | H | C$_3$F$_7$-n | 3-I | 2-Me | 185 |
| 5-8 | C(Me)$_2$CH$_2$SMe | H | C$_5$F$_{11}$-n | 3-I | 2-CH$_2$C$_5$F$_{11}$-n | 173 |
| 5-9 | Pr-i | CF$_3$ | CF$_3$ | 3-I | H | 209 |
| 5-10 | C(Me)$_2$CH$_2$SMe | CF$_3$ | CF$_3$ | 3-I | H | 222 |
| 5-11 | Pr-i | CF$_3$ | CF$_3$ | H | 2-Me | 233 |
| 5-12 | C(Me)$_2$CH=NOMe | CF$_3$ | CF$_3$ | H | 2-Me | 177 |
| 5-13 | C(Me)$_2$CH$_2$SMe | CF$_3$ | CF$_3$ | H | 2-Me | 157 |
| 5-14 | Pr-i | CF$_3$ | CF$_3$ | 3-NO$_2$ | 2-Me | 240 |
| 5-15 | C(Me)$_2$CH$_2$SMe | CF$_3$ | CF$_3$ | 3-NO$_2$ | 2-Me | 227 |
| 5-16 | C(Me)$_2$CH$_2$SMe | CF$_3$ | CF$_3$ | 3-F | 2-Me | 186 |
| 5-17 | Pr-i | CF$_3$ | CF$_3$ | 3-Cl | 2-Me | 212 |
| 5-18 | C(Me)$_2$CH=NOMe | CF$_3$ | CF$_3$ | 3-Cl | 2-Me | 204 |
| 5-19 | C(Me)$_2$CH$_2$SMe | CF$_3$ | CF$_3$ | 3-Cl | 2-Me | 201 |
| 5-20 | C(Me)$_2$CH=NOMe | CF$_3$ | CF$_3$ | 3-Br | 2-Me | 110 |
| 5-21 | Pr-i | CF$_3$ | CF$_3$ | 3-I | 2-Me | 234 |
| 5-22 | Bu-t | CF$_3$ | CF$_3$ | 3-I | 2-Me | 224 |
| 5-23 | C(Me)$_2$CH$_2$C(Me)$_3$ | CF$_3$ | CF$_3$ | 3-I | 2-Me | 92 |
| 5-24 | C(Me)$_2$C≡CH | CF$_3$ | CF$_3$ | 3-I | 2-Me | 208 |
| 5-25 | C(Me)$_2$CH=CHCOOEt | CF$_3$ | CF$_3$ | 3-I | 2-Me | 226 |
| 5-26 | C(Me)$_2$CH=NOMe | CF$_3$ | CF$_3$ | 3-I | 2-Me | 129 |
| 5-27 | C(Me)$_2$CH$_2$OH | CF$_3$ | CF$_3$ | 3-I | 2-Me | 135 |
| 5-28 | C(Me)$_2$CH$_2$SMe | CF$_3$ | CF$_3$ | 3-I | 2-Me | 190 |
| 5-29 | C(Me)$_2$CH$_2$SOMe | CF$_3$ | CF$_3$ | 3-I | 2-Me | 122 |
| 5-30 | C(Me)$_2$CH$_2$SMe | CF$_3$ | CF$_3$ | 3-I | 2-Me | 200 |
| 5-31 | CH(Me)CH$_2$OCON(Me)CH$_2$Ph | CF$_3$ | CF$_3$ | 3-I | 2-Me | 123 |
| 5-32 | CH(Me)CH$_2$OCONHEt | CF$_3$ | CF$_3$ | 3-I | 2-Me | 187 |
| 5-33 | CH(Me)CH$_2$OCONHCH$_2$Ph | CF$_3$ | CF$_3$ | 3-I | 2-Me | 190 |
| 5-34 | CH(Me)CH$_2$OCONH-CH$_2$(2-Me-Ph) | CF$_3$ | CF$_3$ | 3-I | 2-Me | 137 |
| 5-35 | CH(Me)CH$_2$OCONH-CH$_2$(4-CF$_3$-Ph) | CF$_3$ | CF$_3$ | 3-I | 2-Me | 110 |
| 5-36 | CH(Me)CH$_2$OCONH-CH$_2$(4-Me-Ph) | CF$_3$ | CF$_3$ | 3-I | 2-Me | 176 |
| 5-37 | CH(Me)CH$_2$OCONH-CH$_2$(4-Cl-Ph) | CF$_3$ | CF$_3$ | 3-I | 2-Me | 184 |
| 5-38 | CH(Me)CH$_2$OCONH-CH$_2$(4-OMe-Ph) | CF$_3$ | CF$_3$ | 3-I | 2-Me | 186 |
| 5-39 | CH(Me)CH$_2$SMe | CF$_3$ | CF$_3$ | 3-I | 2-Me | 217 |
| 5-40 | C(Me)$_2$CH$_2$NHCOMe | CF$_3$ | CF$_3$ | 3-I | 2-Me | 224 |
| 5-41 | C(Me)$_2$CH$_2$SMe | CF$_3$ | CF$_3$ | 3-CF$_3$ | 2-Me | 206 |
| 5-42 | C(Me)$_2$CH$_2$SOMe | CF$_3$ | CF$_3$ | 3-CF$_3$ | 2-Me | 132 |
| 5-43 | C(Me)$_2$CH$_2$SO$_2$Me | CF$_3$ | CF$_3$ | 3-CF$_3$ | 2-Me | 228 |
| 5-44 | CH(Me)CH$_2$OCON(Et)$_2$ | CF$_3$ | CF$_3$ | 3-CF$_3$ | 2-Me | 186 |
| 5-45 | C(Me)$_2$CH$_2$SMe | CF$_3$ | CF$_3$ | 3,4-Cl$_2$ | 2-Me | 190 |
| 5-46 | Pr-i | CF$_3$ | CF$_3$ | 3-I | 2-Et | 218 |
| 5-47 | C(Me)$_2$CH$_2$SMe | CF$_3$ | CF$_3$ | 3-I | 2-Et | 182 |
| 5-48 | C(Me)$_2$CH$_2$SMe | CF$_3$ | CF$_3$ | 3-I | 2-t-Bu | 192 |
| 5-49 | C(Me)$_2$CH$_2$SOMe | CF$_3$ | CF$_3$ | 3-I | 2-t-Bu | 174 |
| 5-50 | Pr-i | CF$_3$ | CF$_3$ | 3-I | 2-F | 191 |
| 5-51 | Pr-i | CF$_3$ | CF$_3$ | 3-I | 2-Cl | 59 |
| 5-52 | C(Me)$_2$CH$_2$SMe | CF$_3$ | CF$_3$ | 3-I | 2-Cl | 64 |
| 5-53 | C(Me)$_2$CH$_2$SMe | CF$_3$ | CF$_3$ | 3-I | 2-Br | 84 |
| 5-54 | C(Me)$_2$CH$_2$SOMe | CF$_3$ | CF$_3$ | 3-I | 2-Br | 109 |
| 5-55 | C(Me)$_2$CH$_2$SMe | CF$_3$ | CF$_3$ | 3-I | 2-I | 112 |
| 5-56 | C(Me)$_2$CH$_2$SOMe | CF$_3$ | CF$_3$ | 3-I | 2-I | 117 |
| 5-57 | C(Me)$_2$CH$_2$SMe | CF$_3$ | CF$_3$ | 3-I | 2-CN | 96 |
| 5-58 | C(Me)$_2$CH$_2$SOMe | CF$_3$ | CF$_3$ | 3-I | 2-CN | 128 |

TABLE 5-continued

General Formula (I-3)
($Q^1 \sim Q^6, Q^8, Q^9=C, R^2=R^3=H$)

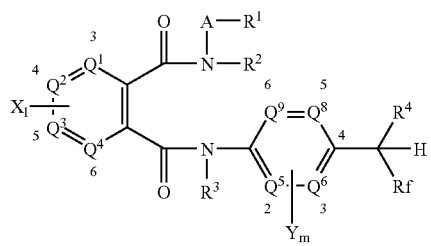

(I-3)

| No. | -A-R$^1$ | R$^4$ | Rf | Xl | Ym | m.p. (°C.) |
|---|---|---|---|---|---|---|
| 5-59 | C(Me)$_2$CH$_2$SO$_2$Me | CF$_3$ | CF$_3$ | 3-I | 2-CN | 214 |
| 5-60 | Pr-i | CF$_3$ | CF$_3$ | 3-I | 2-Me-3-F | 160 |
| 5-61 | C(Me)$_2$CH$_2$SMe | CF$_3$ | CF$_3$ | 3-I | 2-Me-3-F | 204 |
| 5-62 | Pr-i | CF$_3$ | CF$_3$ | 3-I | 2-Me-5-F | 158 |
| 5-63 | C(Me)$_2$CH$_2$SMe | CF$_3$ | CF$_3$ | 3-I | 2-Me-5-F | 199 |
| 5-64 | Pr-i | CF$_3$ | CF$_3$ | 3-I | 2-Me-5-CH$_2$OH | 190 |
| 5-65 | C(Me)$_2$CH$_2$SMe | CF$_3$ | CF$_3$ | 3-I | 2-Me-5-CH$_2$OH | 142 |
| 5-66 | C(Me)$_2$CH$_2$SMe | CF$_3$ | CF$_3$ | 3-I | 2-Me-3-Cl | 148 |
| 5-67 | Pr-i | CF$_3$ | CF$_3$ | 3-I | 2,6-Me$_2$ | 247 |
| 5-68 | C(Me)$_2$CH$_2$SMe | CF$_3$ | CF$_3$ | 3-I | 2,6-Me$_2$ | 136 |
| 5-69 | C(Me)$_2$CH$_2$SMe | CF$_3$ | CF$_3$ | 3-I | 2-CH(Me)CH-(Me)$_2$ | 167 |
| 5-70 | C(Me)$_2$CH$_2$SMe | CF$_3$ | CF$_3$ | 3-I | 3-O-Pr-i | 136 |
| 5-71 | C(Me)$_2$CH$_2$SMe | CF$_3$ | C$_2$F$_5$ | 3-I | 2-Me | 186 |

TABLE 6

($Q^1 \sim Q^6, Q^8, Q^9=C, R^4=Rf=CF_3$)

| No. | —A—R$^1$ | R$^2$ | R$^3$ | Xl | Ym | m.p. (°C.) |
|---|---|---|---|---|---|---|
| 6-1 | Et | Et | H | 3-I | 2-Me | 223 |
| 6-2 | Pr—i | H | Me | 3-I | 2-Me | 232 |
| 6-3 | C(Me)$_2$CH$_2$SMe | H | Me | 3-I | 2-Me | 168 |

TABLE 7

($Q^1 \sim Q^3=C, Q^4=N, Q^5, Q^6, Q^8, Q^9=C$)

| No. | —A—R$^1$ | R$^2$ | R$^3$ | R$^4$ | Rf | Xl | Ym | m.p. (°C.) |
|---|---|---|---|---|---|---|---|---|
| 7-1 | Pr-i | H | H | CF$_3$ | CF$_3$ | H | 2-Me | 157 |

TABLE 8

($Q^1 \sim Q^5=C, Q^6=N, Q^8, Q^9=C, R^4=Rf=CF_3$)

| No. | —A—R$^1$ | R$^2$ | R$^3$ | Xl | Ym | m.p. (°C.) |
|---|---|---|---|---|---|---|
| 8-1 | C(Me)$_2$CH$_2$SMe | H | H | 3-I | H | 239 |
| 8-2 | C(Me)$_2$CH$_2$SOMe | H | H | 3-I | H | 156 |
| 8-3 | C(Me)$_2$CH$_2$SO$_2$Me | H | H | 3-I | H | Amorphous |
| 8-4 | C(Me)$_2$CH$_2$SMe | H | H | 3-I | 2-Cl | Amorphous |
| 8-5 | C(Me)$_2$CH$_2$SOMe | H | H | 3-I | 2-Cl | Amorphous |
| 8-6 | C(Me)$_2$CH$_2$SO$_2$Me | H | H | 3-I | 2-Cl | 229 |
| 8-7 | C(Me)$_2$CH$_2$SMe | H | H | 3-NO$_2$ | 2-Me | 231 |
| 8-8 | C(Me)$_2$CH$_2$SOMe | H | H | 3-NO$_2$ | 2-Me | Amorphous |
| 8-9 | C(Me)$_2$CH$_2$SO$_2$Me | H | H | 3-NO$_2$ | 2-Me | 236 |
| 8-10 | Pr—i | H | H | 3-I | 2-Me | 226 |
| 8-11 | C(Me)$_2$CH$_2$SMe | H | H | 3-I | 2-Me | 159 |
| 8-12 | C(Me)$_2$CH$_2$SOMe | H | H | 3-I | 2-Me | Amorphous |
| 8-13 | C(Me)$_2$CH$_2$SO$_2$Me | H | H | 3-I | 2-Me | 211 |
| 8-14 | CH(Me)CH$_2$SMe | H | H | 3-I | 2-Me | 207 |
| 8-15 | Pr—i | H | H | 3-F | 2-Me | 227-228 |
| 8-16 | CH(Me)CH$_2$SMe | H | H | 3-F | 2-Me | 183-184 |
| 8-17 | C(Me)$_2$CH$_2$SMe | H | H | 3-Br | 2-Me | 204-205 |
| 8-18 | C(Me)$_2$CH$_2$SMe | H | H | 3-I | 6-Me | 178-179 |
| 8-19 | C(Me)$_2$CH$_2$SMe | H | H | 3-I | 2-Br | Amorphous |
| 8-20 | CH(Me)(CH$_2$)$_2$CH$_3$ | H | H | 3-I | 2-Me | 221-222 |
| 8-21 | C(Me)$_2$CH$_2$SMe | H | H | 3-I | 2-OMe | |
| 8-22 | C(Me)$_2$CH$_2$SMe | H | H | 3-I | 2-SMe | |
| 8-23 | C(Me)$_2$CH$_2$SMe | H | H | 3-I | 2,6-Cl$_2$ | 210-212 |
| 8-24 | C(Me)$_2$CH$_2$SMe | H | H | 3-I | 2-Me-6-Cl | 202-203 |

TABLE 8-continued ($Q^1 \sim Q^5$=C, $Q^6$=N, $Q^8$, $Q^9$=C, $R^4$=Rf=$CF_3$)

| No. | —A—$R^1$ | $R^2$ | $R^3$ | Xl | Ym | m.p. (° C.) |
|---|---|---|---|---|---|---|
| 8-25 | CH(Me)CH$_2$OMe | H | H | 3-I | 2-Me | 212-213 |
| 8-26 | CH(Me)CH$_2$OCONHEt | H | H | 3-I | 2-Me | 174-156 |
| 8-27 | CH(Me)CH$_2$OCONH—CH$_2$Ph | H | H | 3-I | 2-Me | 182-184 |
| 8-28 | C(Me)$_2$CH$_2$NHCOMe | H | H | 3-I | 2-Me | Amorphous |
| 8-29 | C(*)H(Me)CH$_2$SMe (S)-enantiomer | H | H | 3-I | 2-Me | 209-210 |
| 8-30 | C(*)H(Me)CH$_2$SO$_2$Me (S)-enantiomer | H | H | 3-I | 2-Me | Amorphous |
| 8-31 | C(Me)$_2$CH$_2$SOMe | H | H | 3-I | 6-Me | Amorphous |
| 8-32 | C(Me)$_2$CH$_2$SO$_2$Me | H | H | 3-I | 6-Me | 135-136 |

TABLE 9

General Formula (I-4)
($Q^1 \sim Q^4$, $Q^6 \sim Q^9$=C, $R^2$=$R^3$=H)

(I-4)

| No. | -A-$R^1$ | $R^4$ | Rf | Xl | Ym | m.p. (° C.) |
|---|---|---|---|---|---|---|
| 9-1 | C(Me)$_2$CH$_2$SMe | CF$_3$ | CF$_3$ | 3-I | 4-Me | 191 |
| 9-2 | C(Me)$_2$CH$_2$SMe | CF$_3$ | CF$_3$ | 3-I | 4-OMe | 189 |
| 9-3 | C(Me)$_2$CH$_2$SMe | CF$_3$ | CF$_3$ | 3-I | 4-SMe | 184 |

TABLE 10

General Formula (I-5)
($Q^1 \sim Q^4$, $Q^5$, $Q^6$, $Q^8$, $Q^9$=C, $R^3$=H)

(I-5)

| No. | -A-$R^1$ | $R^2$ | $R^4$ | Rf | Xl | Ym | m.p. (° C.) |
|---|---|---|---|---|---|---|---|
| 10-1 | Me | Me | CF$_3$ | CF$_3$ | 3-I | 2-Me | 214 |
| 10-2 | CH$_2$SMe | Me | CF$_3$ | CF$_3$ | 3-I | 2-Me | 95 |
| 10-3 | CH$_2$SOMe | Me | CF$_3$ | CF$_3$ | 3-I | 2-Me | 50 |
| 10-4 | CH$_2$SO$_2$Me | Me | CF$_3$ | CF$_3$ | 3-I | 2-Me | 60 |

In Table 8, physical property of some compounds are expressed in the term of "Amorphous". $^1$H-NMR data of these compounds are shown in Table 11.

TABLE 11

| No. | NMR $^1$H-NMR[CDCl$_3$/TMS, δ (ppm)] |
|---|---|
| 8-3 | 1.78(s.6H), 2.81(s.3H), 3.67(s.2H), 4.32(m.1H) 6.30(br.1H), 7.23(m.2H), 7.66(d.1H), 7.82(d.1H) 8.24(dd.1H), 8.67(d.1H), 9.69(br.1H) |
| 8-4 | 1.47(s.6H), 1.90(s.3H), 2.91(s.2H), 4.37(m.1H) 5.90(br.1H), 7.23(m.1H), 7.54(d.1H), 7.77(d.1H) 8.02(dd.1H), 8.96(d.1H), 9.02(br.1H) |
| 8-5 | 1.63(s.3H), 1.66(s.3H), 2.39(s.3H), 2.87(d.1H) 3.28(d.1H), 4.37(m.1H), 6.79(br.1H), 7.24(m.1H) 7.57(d.1H), 7.73(d.1H), 8.03(dd.1H), 8.83(d.1H) 9.03(br.1H) |
| 8-8 | 1.56(s.3H), 1.61(s.3H), 2.34(s.3H), 2.61(s.3H) 2.90(s.2H), 4.45(m.1H), 7.24(br.1H), 7.48(d.1H) 7.71(m.1H), 8.11(d.1H), 8.29(d.1H), 8.72(d.1H) 8.76(br.1H) |
| 8-12 | 1.58(s.3H), 1.63(s.3H), 2.24(s.3H), 2.58(s.3H) 2.87(d.1H), 3.04(d.1H), 4.39(m.1H), 6.87(br.1H) 7.23(m.1H), 7.44(d.1H), 7.76(d.1H), 7.99(d.1H) 8.56(br.1H), 8.83(d.1H) |
| 8-19 | 1.47(s.6H), 1.91(s.3H), 2.91(s.2H), 4.39(m.1H), 5.95(br.1H), 7.22(m.1H), 7.53(d.1H), 7.74(d.1H), 8.01(d.1H), 8.86(br.1H), 8.91(d.1H) |
| 8-28 | 1.37(s.6H), 1.87(s.3H), 2.56(s.3H), 3.53(s.2H) 4.40(m.1H) 6.19(br.1H), 7.18(br.1H), 7.21(m.2H) 7.69(d.1H), 7.84(d.1H), 7.89(d.1H), 9.34(br.1H) |
| 8-30 | 1.52(d.3H), 2.58(s.3H), 2.76(s.3H), 3.18(m.1H) 3.37(rn.1H), 4.39(m.1H), 4.63(m.1H), 6.65(d.1H) 7.24(m.1H), 7.41(d.1H), 7.74(d.1H), 7.99(d.1H) 8.30(br.1H), 8.52(d.1H) |
| 8-31 | 1.58(s.3H), 1.64(s.3H), 2.28(s.3H), 2.39(s.3H), 2.93(d.1H), 2.97(d.1H), 4.48(m.1H), 7.02(br.1H), 7.20(m.1H), 7.38(s.1H), 7.75(d.1H), 7.96(d.1H), 8.75(br.1H), 9.26(s.1H) |

Next, typical examples of the present invention are presented below. The present invention is by no means limited by these examples.

EXAMPLE 1

Production of N$^2$-(1,1-dimethyl-2-methylthioethyl)-3-iodo-N$^1$-{2-methyl-4-[2,2,2-trifluoro-1-(trifluoromethyl)ethyl]phenyl}phthalamide (Compound No. 5-28)

(1-1) To 30 ml of tetrahydrofuran (THF) was added 0.5 g (13.2 mmol) of lithium aluminum hydride. While keeping the resulting suspension at a temperature of 0° C., a solution of 13.8 g (20 mmol) of 2-methyl-4-[1,2,2,2-tetrafluoro-1-(trifluoromethyl)ethyl]aniline in 20 ml of THF was dropped into the suspension with stirring over a period of 15 minutes. After completion of the dropping, the resulting mixture was stirred at room temperature for 30 minutes, and then heated under reflux for one hour to make progress a reaction. The reaction mixture was poured into ice water, 20 ml of 1N-aqueous solution of sodium hydroxide was added, and the resulting mixture was stirred. The mixture was extracted with 50 ml of methyl tert-butyl ether, the organic layer was dried on anhydrous magnesium sulfate and concentrated under reduced pressure, and the residue was purified by distillation under reduced pressure. Thus, 11.4 g (yield: 89%) of 2-methyl-4-[2,2,2-trifluoro-1-(trifluoromethyl)ethyl]aniline (Compound No. 1-3) was obtained as a fraction having a boiling point of 103° C. (6 mmHg). (1-2) In 10 ml of acetonitrile was dissolved 750 mg (2.0 mmol) of N-(1,1-dimethyl-2-methylthioethyl)-6-iodophthalic acid isoimide, to which were added 515 mg (2.0 mmol) of 2-methyl-4-[2,2,2-trifluoro-1-(trifluoromethyl)ethyl]aniline and 10 mg of trifluoroacetic acid. The mixture was stirred at room temperature for 2 hours. The deposited crystal was collected by filtration and washed with a small quantity of ether. Thus, 1.0 g of the objective compound was obtained (yield: 79%).

EXAMPLE 2

Production of $N^2$-(1,1-dimethyl-2-methylsulfinyl ethyl)-3-iodo-$N^1$-[2-methyl-4-{2,2,2-trifluoro-1-(trifluoromethyl)ethyl}phenyl]phthalamide (Compound No. 5-29)

In 10 ml of chloroform was dissolved 0.63 g (1.0 mmol) of $N^2$-(1,1-dimethyl-2-methylthioethyl)-3-iodo-$N^1$-{2-methyl-4-[2,2,2-trifluoro-1-(trifluoromethyl)ethyl]phenyl}phthalamide, and the resulting solution was cooled to 0° C. To the solution was added 0.19 g (1.1 mmol) of meta-chloroperbenzoic acid. After stirring for one hour, the reaction mixture was washed with 10% aqueous solution of potassium carbonate and dried on anhydrous magnesium sulfate, and the solvent was dissolved off under reduced pressure. Thus, 0.45 g of the objective compound was obtained (yield: 69%).

EXAMPLE 3

Production of $N^2$-(1,1-dimethyl-2-methylthioethyl)-3-iodo-$N^1$-{2-chloro-6-[2,2,2-trifluoro-1-(trifluoromethyl)ethyl]pyridin-3-yl}phthalamide (Compound No. 8-4)

(3-1) In 80 ml of DMSO was suspended 2.84 g (75.0 mmol) of sodium borohydride, to which was added 3.93 g (15 mmol) of 5-amino-2-[1,2,2,2-tetrafluoro-1-(trifluoromethyl)ethyl]pyridine with stirring. The mixture thus obtained was stirred at room temperature for 50 hours. The reaction mixture was slowly poured into ice water to decompose the excessive sodium borohydride. After extraction with 50 ml of ethyl acetate, the organic layer was washed three times with water and then once with saturated aqueous solution of sodium chloride, dried over anhydrous magnesium sulfate, and then concentrated under reduced pressure. The residue was separated and purified by silica gel column chromatography (hexane/ethyl acetate=4:1). Thus, 1.0 g of 5-amino-2-[2,2,2-trifluoro-1-(trifluoromethyl)ethyl]pyridine (Compound No. 3-1) was obtained (yield: 27%).

(3-2) In 10 ml of acetonitrile was dissolved 0.56 g (2.3 mmol) of 5-amino-2-[2,2,2-trifluoro-1-(trifluoromethyl)ethyl]pyridine, to which was added 0.31 g (2.3 mmol) of N-chlorosuccinimide (NCS). The mixture thus obtained was heated under reflux for one hour to make progress a reaction. The solvent was distilled off under reduced pressure, and the residue was separated and purified by silica gel column chromatography (hexane/ethyl acetate=2:1) to obtain 0.55 g of 3-amino-2-chloro-6-[2,2,2-trifluoro-1-(trifluoromethyl)ethyl]pyridine (Compound No. 4-2) (yield: 86%).

(3-3) In 10 ml of acetonitrile was dissolved 750 mg (2.0 mmol) of N-(1,1-dimethyl-2-methylthioethyl)-6-iodophthalic acid isoimide. To the solution were added 0.55 g (2.0 mmol) of 3-amino-2-chloro-6-[2,2,2-trifluoro-1-(trifluoromethyl)ethyl]pyridine and 10 mg of trifluoroacetic acid. The mixture thus obtained was stirred at room temperature for 10 hours. The reaction mixture was poured into ice water, and the phase of reaction mixture was washed with saturated aqueous solution of sodium bicarbonate and dried on anhydrous magnesium sulfate. The solvent was distilled off under reduced pressure, and the residue was separated and purified by silica gel column chromatography (hexane/ethyl acetate=4:1) to obtain 0.83 g of the objective compound (yield 63%).

EXAMPLE 4

Production of 3-iodo-2-(4,4-dimethyloxazolin-2-yl)-2'-methyl-4'-[2,2,2-trifluoro-1-(trifluoromethyl) ethyl]benzanilide (Compound No. 10-1)

In pyridine was dissolved 1.1 g (1.8 mmol) of 3-iodo-$N^1$-(2-methyl-4-[2,2,2-trifluoro-1-(trifluoromethyl)ethyl]phenyl-$N^2$-(2-hydroxy-1,1-dimethylethyl)phthalamide. To the solution was added 0.25 g (2.2 mmol) of methanesulfonyl chloride. The mixture thus obtained was stirred at room temperature for 8 hours and then concentrated under reduced pressure. The residue was diluted with ethyl acetate and washed with water, the organic layer was dried on anhydrous magnesium sulfate, the solvent was distilled off under reduced pressure, and the residue was separated and purified by silica gel column chromatography (hexane/ethyl acetate=2:1). Thus, 0.64 g of the objective compound was obtained (yield 60%).

The agrohorticultural insecticide, containing the substituted aromatic amide derivative represented by the formula (I) or salt thereof of the present invention as an active ingredient, are suitable for controlling various insect pests such as agrohorticultural insect pests, stored grain insect pests, sanitary insect pests, nematodes, etc., which are injurious to paddy rice, fruit trees, vegetables, other crops, flowers, ornamental plants, etc. They have a marked insecticidal effect, for example, on LEPIDOPTERA including summer fruit tortrix (*Adoxophes orana fasciata*), smaller tea tortrix (*Adoxophyes* sp.), Manchurian fruit moth (*Grapholita inopinata*), oriental fruit moth (*Grapholita molesta*), soybean pod border (*Leguminovora glycinivorella*), mulberry leafroller (*Olethreutes mori*), tea leafroller (*Caloptilia thevivora*), *Caloptilia* sp. (*Caloptilia zachrysa*), apple leafminer (*Phyllonorycter ringoniella*), pear barkminer (*Spulerrina astaurota*), common white (*Piers rapae crucivora*), tobacco budworm (*Heliothis* sp.), codling moth (*Laspey resia pomonella*), diamondback moth (*Plutella xylostella*), apple fruit moth (*Argyresthia conjugella*), peach fruit moth (*Carposina niponensis*), rice stem borer (*Chilo suppressalis*), rice leafroller (*Cnaphalocrocis medinalis*), tobacco moth (*Ephestia elutella*), mulberry pyralid (*Glyphodes pyloalis*), yellow rice borer (*Scirpophaga incertulas*), rice skipper (*Parnara guttata*), rice armyworm (*Pseudaletia separata*), pink borer (*Sesamia inferens*), common cutworm (*Spodoptera litura*), beet armyworm (*Spodoptera exigua*), etc.; HEMIPTERA including aster leafhopper (*Macrosteles fascifrons*), green rice leafhopper (*Nephotettix cincticeps*), brown rice planthopper (*Nilaparvata lugens*), whitebacked rice planthopper (*Sogatella furcifera*), citrus psylla (*Diaphorina citri*), grape whitefly (*Aleurolibus taonabae*), sweetpotato whitefly (*Bemisia tabaci*), greenhouse whitefly (*Trialeurodes vaporariorum*), turnup aphid (*Lipaphis erysimi*), green peach aphid (*Myzus persicae*), Indian wax scale (*Ceroplastes ceriferus*), cottony citrus scale (*Pulvinaria aurantii*), camphor scale (*Pseudaonidia duplex*), san Jose scale (*Comstockaspis perniciosa*), arrowhead scale (*Unapsis yanonensis*), etc.; TYLENCHIDA including soybean beetle (*Anomala rufocuprea*), Japanese beetle (*Popillia japonica*), tobacco beetle (*Lasioderma serricorne*), powderpost beetle (*Lyctus brunneus*), twenty-eight-spotted ladybird (*Epilachna vigintiotopunctata*), azuki bean weevil (*Callosobruchus chinensis*), vegetable weevil (*Listroderes costirostris*), maize weevil (*Sitophilus zeamais*), boll weevil (*Anthonomus gradis gradis*), rice water weevil (*Lissorhoptrus oryzophilus*), cucurbit leaf beetle (*Aulacophora femoralis*), rice leaf beetle (*Oulema oryzae*), striped flea beetle (*Phyllotreta striolata*), pine shoot beetle (*Tomicus piniperda*), Colorado potato beetle (*Leptinotarsa decemlineata*), Mexican bean beetle (*Epilachna varivestis*), corn rootworm (*Diabrotica* sp.), etc.; DIPTERA including (*Dacus(Zeugodacus) cucurbitae*), oriental fruit fly (*Dacus(Bactrocera) dorsalis*), rice leafminer (*Agnomyza oryzae*), onion maggot (*Delia antiqua*), seedcorn maggot (*Delia platura*), soybean pod gall midge (*Asphondylia* sp.), muscid fly (*Musca domestica*), house mosquito (*Culex pipiens pipiens*), etc.; TYLENCHIDA including root-lesion nematode (*Pratylenchus* sp.), coffee root-lesion nematode (*Pratylenchus coffeae*), potato cyst nematode (*Globodera rostochiensis*), root-knot nematode (Meloidogyne sp.), citrus nematode (*Tylenchulus semipenetrans*), *Aphelenchus* sp. (*Aphelenchus avenae*), chrysanthemum foliar (*Aphelenchoides ritzemabosi*), etc.; and ACARINA including citrus red mite (*Panonychus citri*), fruit tree red spider mite (*Panonychus ulmi*), carmine spider mite (*Tetranychus cinnabarinus*), Kanzawa spider mite (*Tetranychus Kanzawai Kishida*), two-spotted spider mite (*Tetranychus urticae Koch*), pink tea rust mite (*Acaphylla theae*), pink citrus rust mite (*Aculops pelekassi*), purple tea mice (*Calacarus carinatus*), pear rust mite (*Epitrimerus* sp.), etc.

The agrohorticultural insecticide, containing the substituted aromatic amide derivative represented by formula (I) or salt thereof of the present invention, has a marked controlling effect on the above-exemplified insect pests, sanitary pests and/or nematodes, which are injurious to paddy field crops, upland crops, fruit trees, vegetables and other crops, flowers and ornament plants, and the like. Therefore, the desired effect of the agrohorticultural insecticide of the present invention can be exhibited by applying the insecticide to the nursery facility, paddy field water, stalks and leaves or soil of paddy field, upland field, fruit trees, vegetables, other crops or flowers and ornament plants at a season at which the insect pests, sanitary pests or nematodes are expected to appear, before their appearance or at the time when their appearance is confirmed. Particularly, a preferable application for using the agrohorticultural insecticide of the present invention is the application for which both of "penetration and translocation" are utilized, wherein the present agrohorticultural insecticide is applied to the nursery soil of crops, ornamental plants or the like; the picking-in hole soil at a transplantation; the plant roots; the irrigation water; or the cultural water of a water culture; so as to uptake the substituted aromatic amide derivatives of the present invention from the roots through or not through the soil.

In general, the agrohorticultural insecticide of the present invention is used after being prepared into conveniently usable forms according to ordinary manner for preparation of agrochemicals.

That is, the substituted aromatic amide derivative of formula (I) or salt thereof and an appropriate carrier are blended optionally together with an adjuvant in a proper proportion and prepared into a suitable preparation form such as suspension, emulsifiable concentrate, soluble concentrate, wettable powder, granules, dust or tablets through dissolution, separation, suspension, mixing, impregnation, adsorption or sticking.

The inert carrier used in the present invention may be either solid or liquid. As the solid carrier, soybean flour, cereal flour, wood flour, bark flour, saw dust, powdered tobacco stalks, powdered walnut shells, bran, powdered cellulose, extraction residues of vegetables, powdered synthetic polymers or resins, clay (e.g. kaolin, bentonite and acid clay), talc (e.g. talc and pyrophyllite), silica materials (e.g. diatomaceous earth, siliceous sand, mica, white carbon, i.e. synthetic high-dispersion silicic acid, also called finely divided hydrated silica or hydrated silicic acid, some of the commercially available products contain calcium silicate as the major component), activated carbon, powdered sulfur, pumice, calcined diatomaceous earth, ground brick, fly ash, sand, calcium carbonate, calcium phosphate and other inorganic or mineral powders, chemical fertilizers such as ammonium sulfate, ammonium phosphate, ammonium nitrate, urea, ammonium chloride and the like, and compost. These carriers may be used either alone or as a mixture of two or more carriers.

The liquid carrier is that which itself has a solubility or which is without such solubility but is capable of dispersing an active ingredient with the aid of an adjuvant. The following are typical examples of the liquid carrier and can be used alone or as a mixture thereof. Water; alcohols such as methanol, ethanol, isopropanol, butanol and ethylene glycol; ketones such as acetone, methyl ethyl ketone, methyl isobutyl ketone, diisobutyl ketone and cyclohexanone; ethers such as ethyl ether, dioxane, cellosolve, dipropyl ether and tetrahydrofuran; aliphatic hydrocarbons such as kerosene and mineral oil; aromatic hydrocarbons such as benzene, toluene, xylene, solvent naphtha and alkylnaphthalene; halogenated hydrocarbons such as dichlorethane, chloroform, carbon tetrachloride and chlorobenzene; esters such as ethyl acetate, diisopropyl phthalate, dibutyl phthalate and dioctyl phthalate; amides such as dimethylformamide, diethylformamide and dimethylacetamide; nitriles such as acetonitrile; and dimethyl sulfoxide.

The following are typical examples of the adjuvant, which are used depending upon purposes and used alone or in combination of two or more adjuvants in some cases, or need not to be used at all.

To emulsify, disperse, dissolve and/or wet an active ingredient, a surfactant is used. As the surfactant, there can be exemplified polyoxyethylene alkyl ethers, polyoxyethylene alkylaryl ethers, polyoxyethylene higher fatty acid esters, polyoxyethylene resinates, polyoxyethylene sorbitan monolaurate, polyoxyethylene sorbitan monooleate, alkylarylsulfonates, naphthalene-sulfonic acid condensation products, ligninsulfonates and higher alcohol sulfate esters.

Further, to stabilize the dispersion of an active ingredient, tackify it and/or bind it, there may be used adjuvants such as casein, gelatin, starch, methyl cellulose, carboxymethyl cellulose, gum arabic, polyvinyl alcohols, turpentine, bran oil, bentonite and ligninsulfonates.

To improve the flowability of a solid product, there may be used adjuvants such as waxes, stearates and alkyl phosphates.

Adjuvants such as naphthalenesulfonic acid condensation products and polycondensates of phosphates may be used as a peptizer for dispersible products.

Adjuvants such as silicone oil may also be used as a defoaming agent.

The content of the active ingredient may be varied according to the need, thus, it can be properly selected from the range between 0.01 and 90% by weight in terms of 100% by weight of the agrohorticultural insecticide of the present invention. For example, in dusts or granules, the suitable content thereof is from 0.01 to 50% by weight. In emulsifiable concentrate and flowable wettable powder, too, the suitable content is from 0.01 to 50% by weight.

The agrohorticultural insecticide of the present invention is used to control a variety of insect pests in the following manner. That is, it is applied to a crop on which the insect pests are expected to appear or a site where appearance of the insect pests is undesirable, as it is or after being properly diluted with or suspended in water or the like, in an amount effective for control of the insect pests.

The applying dosage of the agrohorticultural insecticide of the present invention is varied depending upon various factors such as a purpose, insect pests to be controlled, a growth state of a plant, tendency of insect pests appearance, weather, environmental conditions, a preparation form, an application method, an application site and an application time. It may be properly chosen in a range of 0.001 g to 10 kg, preferably 0.01 g to 1 kg (in terms of active ingredient compound) per 10 ares depending upon purposes.

The agrohorticultural insecticide of the present invention may be used in admixture with other agrohorticultural insecticides, acaricides, nematocides, fungicides or biological pesticides, in order to expand both spectrum of controllable diseases and insect pest species and the period of time when effective applications are possible or to reduce the dosage. Of course, the agrohorticultural insecticide of the present invention may be used in admixture with herbicides, plant growth regulators, fertilizer and the like, depending on the scene where the present agrohorticultural insecticide of the present invention is applied to.

Next, typical formulations and test examples of the invention are presented below. The present invention is by no means limited by these examples.

As used in the examples, the terms "part" and "parts" are by weight.

FORMULATION EXAMPLE 1

| Each compound listed in Tables 5 to 10 | 10 parts |
| Xylene | 70 parts |
| N-methylpyrrolidone | 10 parts |
| Mixture of polyoxyethylene nonylphenyl ether and calcium alkylbenzenesulfonate | 10 parts |

An emulsifiable concentrate was prepared by mixing uniformly the above ingredients to effect dissolution.

FORMULATION EXAMPLE 2

| Each compound listed in Tables 5 to 10 | 3 parts |
| Clay powder | 82 parts |
| Diatomaceous earth powder | 15 parts |

A dust was prepared by mixing uniformly and grinding the above ingredients.

FORMULATION EXAMPLE 3

| Each compound listed in Tables 5 to 10 | 5 parts |
| Mixed powder of bentonite and clay | 90 parts |
| Calcium ligninsulfonate | 5 parts |

Granules were prepared by mixing the above ingredients uniformly, and kneading the resulting mixture together with a suitable amount of water, followed by granulation and drying.

FORMULATION EXAMPLE 4

| Each compound listed in Tables 5 to 10 | 20 parts |
| Mixture of kaolin and synthetic high-dispersion silicic acid | 75 parts |
| Mixture of polyoxyethylene nonylphenyl ether and calcium alkylbenzenesulfonate | 5 parts |

A wettable powder was prepared by mixing uniformly and grinding the above ingredients.

TEST EXAMPLE 1

Insecticidal Effect on Diamond Back Moth (*Plutella xylostella*)

Adult diamond back moths were released and allowed to oviposit on a Chinese cabbage seedling. Two days after the release, the seedling having the eggs deposited thereon was immersed for about 30 seconds in a liquid chemical prepared by diluting a preparation containing each compound listed in Tables 4 to 9 as an active ingredient to adjust the concentration to 50 ppm. After air-dryness, it was allowed to stand in a room thermostatted at 25° C. Six days after the immersion, the hatched insects were counted. The mortality was calculated according to the following equation and the insecticidal effect was judged according to the criterion shown below. The test was carried out with triplicate groups of 10 insects.

$$\text{Corrected mortality}(\%) = \frac{\begin{array}{c}\text{Number of}\\\text{hatched insects}\\\text{in untreated group}\end{array} - \begin{array}{c}\text{Number of}\\\text{hatched insects}\\\text{in treated group}\end{array}}{\begin{array}{c}\text{Number of}\\\text{hatched insects}\\\text{in untreated group}\end{array}} \times 100$$

Criterion:
A—Mortality 100%
B—Mortality 99-90%
C—Mortality 89-80%
D—Mortality 79-50%
E—Mortality 49% or less
-—no test The result is shown in Table 12 below.

TEST EXAMPLE 2

Insecticidal Effect on Common Cutworm (*Spodoptera litura*)

A piece of cabbage leaf (cultivar; Shikidori) was immersed for about 30 seconds in a liquid chemical prepared by diluting a preparation containing each compound listed in Tables 4 to 9 as an active ingredient to adjust the concentration to 50 ppm. After air-dryness, it was placed in a plastic Petri dish with a diameter of 9 cm and inoculated with second-instar larvae of common cutworm, after which the dish was closed and then allowed to stand in a room thermostatted at 25° C. Eight days after the inoculation, the dead and alive were counted. The mortality was calculated according to the following equation and the insecticidal effect was judged according to the criterion shown in Test Example 1. The test was carried out with triplicate groups of 10 insects.

$$\text{Corrected mortality}(\%) = \frac{\begin{array}{c}\text{Number of} \\ \text{alive larvae in} \\ \text{untreated group}\end{array} - \begin{array}{c}\text{Number of} \\ \text{alive larvae in} \\ \text{treated group}\end{array}}{\begin{array}{c}\text{Number of} \\ \text{alive larvae in} \\ \text{untreated group}\end{array}} \times 100$$

The result is shown in Table 12 below.

TEST EXAMPLE 3

Insecticidal Effect on Smaller Tea Tortrix (*Adxophyes* sp.)

Tea leaves were immersed for about 30 seconds in a liquid chemical prepared by diluting a preparation containing each compound listed in Tables 1 to 3 as an active ingredient to adjust the concentration to 50 ppm. After air-dryness, the tea leaves were placed in a plastic Petri dish with a diameter of 9 cm and inoculated with larvae of smaller tea tortrix, after which the dish was allowed to stand in a room thermostatted at 25° C. and having a humidity of 70%. Eight days after the inoculation, the dead and alive were counted and the insecticidal effect was judged according to the criterion shown in Test Example 1. The test was carried out with triplicate groups of 10 insects.

The result is shown in Table 12 below.

TABLE 12

| No. | Test Example 1 | Test Example 2 | Test Example 3 |
|---|---|---|---|
| 5-1 | A | A | A |
| 5-2 | A | A | A |
| 5-3 | A | A | A |
| 5-4 | A | A | A |
| 5-5 | A | A | A |
| 5-6 | A | A | A |
| 5-7 | A | A | A |
| 5-8 | A | A | A |
| 5-9 | A | A | A |
| 5-10 | A | A | A |
| 5-11 | A | E | A |
| 5-12 | A | E | A |
| 5-13 | A | E | E |
| 5-14 | A | A | A |
| 5-15 | A | A | A |
| 5-16 | A | A | A |
| 5-17 | A | A | A |
| 5-18 | A | A | A |
| 5-19 | A | A | A |
| 5-20 | A | A | A |
| 5-21 | A | A | A |
| 5-22 | A | C | A |
| 5-23 | A | — | A |
| 5-24 | A | C | A |
| 5-25 | A | A | A |
| 5-26 | A | C | A |
| 5-27 | A | E | E |
| 5-28 | A | A | A |
| 5-29 | A | A | A |
| 5-30 | A | A | A |
| 5-31 | A | A | A |
| 5-32 | A | A | A |
| 5-33 | A | A | A |
| 5-34 | A | A | A |
| 5-35 | A | A | A |
| 5-36 | A | E | A |
| 5-37 | A | A | A |
| 5-38 | A | A | A |
| 5-39 | A | A | A |
| 5-40 | A | A | A |
| 5-41 | A | A | A |
| 5-42 | A | A | A |
| 5-43 | A | A | A |
| 5-44 | A | A | A |
| 5-45 | A | A | A |
| 5-46 | A | A | A |
| 5-47 | A | A | A |
| 5-48 | A | E | E |
| 5-49 | A | E | E |
| 5-50 | A | A | A |
| 5-51 | A | A | A |
| 5-52 | A | A | A |
| 5-53 | A | A | A |
| 5-54 | A | A | A |
| 5-55 | A | A | A |
| 5-56 | A | C | A |
| 5-57 | A | A | A |
| 5-58 | A | A | A |
| 5-59 | A | A | A |
| 5-60 | A | A | A |
| 5-61 | A | A | A |
| 5-62 | A | A | A |
| 5-63 | A | A | A |
| 5-66 | A | A | A |
| 5-67 | A | E | A |
| 5-68 | A | E | E |
| 5-70 | A | E | E |
| 5-71 | A | A | A |
| 6-1 | A | A | A |
| 6-2 | A | E | A |
| 6-3 | A | A | A |
| 7-1 | A | E | A |
| 8-1 | A | C | E |
| 8-2 | A | E | E |
| 8-3 | A | E | A |
| 8-4 | A | A | A |
| 8-5 | A | A | A |
| 8-6 | A | D | A |
| 8-7 | A | C | E |
| 8-8 | A | E | E |
| 8-9 | A | D | E |
| 8-10 | A | A | A |
| 8-11 | A | A | A |
| 8-12 | A | A | A |
| 8-13 | A | A | A |
| 8-14 | A | A | A |
| 8-26 | A | D | A |
| 8-27 | A | E | E |
| 10-1 | A | E | E |
| 10-2 | A | E | E |
| 10-3 | A | E | E |
| 10-4 | A | E | E |

TEST EXAMPLE 4

Controlling Effect on Diamond Back Moth (*Plutella xylostella*) with Soil Treatment of Olive The pricking-in hole treatment was done with the granules containing each compound listed in Tables 4 according to the formulation examples of the present invention, at the fix planting of olive (cultivar; YR Seitoku). Nine days after the fix planting, about 50 eggs of diamond back moth (*Plutella xylostella*) were innoculated, then the number of the parasitic insects of diamond back moth (*Plutella xylostella*) was counted on the specified days after the innoculation.

The result is shown in Table 13 below.

TABLE 13

| No. | Dosage mgAI/plant | Number of the parasitic insects/three plants | | |
|---|---|---|---|---|
| | | After 18 days | After 25 days | After 32 days |
| 5-28 | 10 | 0 | 5 | 14 |
| 5-29 | 10 | 0 | 0 | 0 |
| 5-30 | 10 | 0 | 3 | 22 |
| A | 10 | 10 | 60 | — |
| B | 10 | 40 | 43 | — |
| C | 10 | 56 | 80 | — |
| Untreated area | — | 47 | 64 | 82 |

The active ingredient of the comparative compounds were as follows:

A: Compound No. 372 disclosed in JP-A-11-240857,

B: Compound No. 122 disclosed in JP-A-2001-131141 and

C: Compound No. 124 disclosed in JP-A-2001-131141.

As is clearly indicated in Table 13, in case of treating the soil with the present compound, it exhibited the excellent controlling effect even after 32 days.

On the other hand, many parasite insects were observed after 18 days in the olive treated with the comparative compounds disclosed in JP-A-11-240857 and JP-A-2001-131141, and the controlling effects of the comparative compounds were clearly inferior to that of the present compound already after 25 days.

The invention claimed is:

1. A compound represented by formula (I):

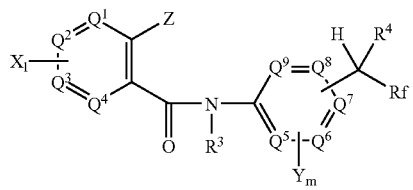

{wherein Z represents formula (II):

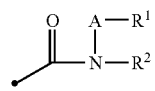

(wherein A, $R^1$ and $R^2$ are as defined below), or formula (III):

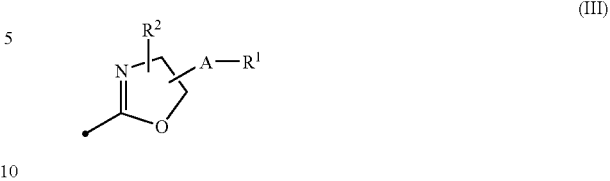

(wherein A represents a $C_1$-$C_6$ alkylene group; a substituted $C_1$-$C_6$ alkylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; a $C_2$-$C_6$ alkenylene group, a substituted $C_2$-$C_6$ alkenylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; a $C_2$-$C_6$ alkynylene group; or a substituted $C_3$-$C_6$ alkynylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; and an arbitrarily selected saturated carbon atom in the $C_1$-$C_6$ alkylene group, substituted $C_1$-$C_6$ alkylene group, $C_3$-$C_6$ alkenylene group, substituted $C_3$-$C_6$ alkenylene group, $C_3$-$C_6$ alkynylene group or substituted $C_3$-$C_6$ alkynylene group may be substituted with a $C_2$-$C_5$ alkylene group to form a $C_3$-$C_6$ cycloalkane ring, and arbitrarily selected two carbon atoms in the $C_2$-$C_6$ alkylene group, substituted $C_2$-$C_6$ alkylene group, $C_3$-$C_6$ alkenylene group or substituted $C_3$-$C_6$ alkenylene group may be taken conjointly with an alkylene group or an alkenylene group to form a $C_3$-$C_6$ cycloalkane ring or a $C_3$-$C_6$ cycloalkene ring;

$R^1$ represents a hydrogen atom; a halogen atom; a cyano group; a nitro group; a $C_3$-$C_6$ cycloalkyl group; a $C_1$-$C_6$ alkoxycarbonyl group; a mono $C_1$-$C_6$ alkylaminocarbonyl group; a di $C_1$-$C_6$ alkylaminocarbonyl group which the $C_1$-$C_6$ alkyl groups may be the same or different; a mono $C_1$-$C_6$ alkylaminosulfonyl group; a di $C_1$-$C_6$ alkylaminosulfonyl group which the $C_1$-$C_6$ alkyl groups may be the same or different, a di $C_1$-$C_6$ alkoxyphosphoryl group which the $C_1$-$C_6$ alkyl groups may be the same or different, a di $C_1$-$C_6$ alkoxythiophosphoryl group which the $C_1$-$C_6$ alkyl groups may be the same or different; —$C(R^5)$=$NOR^6$ (in this formula, $R^5$ represents a hydrogen atom or a $C_1$-$C_6$ alkyl group; and $R^6$ represents a hydrogen atom; a $C_1$-$C_6$ alkyl group; a $C_3$-$C_6$ alkenyl group; a $C_3$-$C_6$ alkynyl group; a $C_3$-$C_6$ cycloalkyl group; a phenyl $C_1$-$C_4$ alkyl group; or a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group and $C_1$-$C_6$ alkylthio group); a phenyl group; a substituted phenyl group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group; a substituted heterocyclic group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^1$-$R^7$ (in this formula, $A^1$ represents —O—, —S—, —SO—, —$SO_2$— or —N($R^6$)— (in this formula, $R^6$ is as defined above); and $R^7$ represents a hydrogen atom; a $C_1$-$C_6$ alkyl group; a halo $C_1$-$C_6$ alkyl group; a $C_3$-$C_6$ alkenyl group; a halo $C_3$-$C_6$ alkenyl group; a $C_3$-$C_6$ alkynyl group; a halo $C_3$-$C_6$ alkynyl group; a $C_3$-$C_6$ cycloalkyl group; a phenyl group; a substituted phenyl group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a phenyl $C_1$-$C_4$ alkyl group; a substituted phenyl $C_1$-$C_4$ alkyl group having, on the ring thereof, at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a heterocyclic group; a substituted heterocyclic group having, on the ring thereof, at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a $C_1$-$C_6$ alkylcarbonyl group; a halo $C_1$-$C_6$ alkylcarbonyl group; a $C_1$-$C_6$ alokoxycarbonyl group; a mono $C_1$-$C_6$ alkylaminocarbonyl group; a di $C_1$-$C_6$ alkylaminocarbonyl group which the $C_1$-$C_6$ alkyl groups may be the same or different; a $C_1$-$C_6$ alkylsulfonyl group; a halo $C_1$-$C_6$ alkylsulfonyl group; a mono $C_1$-$C_6$ alkylaminosulfonyl group; a di $C_1$-$C_6$ alkylaminosulfonyl group which the $C_1$-$C_6$ alkyl groups may be the same or different; a di $C_1$-$C_6$ alkoxyphosphoryl group which the $C_1$-$C_6$ alkyl groups may be the same or different; or a di $C_1$-$C_6$ alkoxythiophosphoryl group which the $C_1$-$C_6$ alkyl groups may be the same or different);

$R^2$ represents a hydrogen atom; a $C_1$-$C_4$ alkyl group; a $C_1$-$C_4$ alkoxy $C_1$-$C_4$ alkyl group; or a $C_1$-$C_4$ alkylthio $C_1$-$C_4$ alkyl group; and $R^2$ may be taken conjointly together with A or $R^1$ to form one to three, the same or different, 5- to 7-membered rings which may be intercepted by oxygen atom, sulfur atom or nitrogen atom);

$R^3$ represents a hydrogen atom; a $C_1$-$C_4$ alkyl group; a $C_1$-$C_4$ alkoxy $C_1$-$C_4$ alkyl group; or a $C_1$-$C_4$ alkylthio $C_1$-$C_4$ alkyl group;

$R^4$ represents a fluoro $C_1$-$C_6$ alkyl group; and Rf represents a fluoro $C_1$-$C_6$ alkyl group;

$Q^1$ to $Q^6$, $Q^8$ and $Q^9$ represent a carbon atom;

X which may be the same or different represent a halogen atom; a nitro group; a cyano group; a $C_1$-$C_6$ alkyl group; a halo $C_1$-$C_6$ alkyl group; a $C_2$-$C_6$ alkenyl group; a halo $C_2$-$C_6$ alkenyl group; a $C_2$-$C_6$ alkynyl group; a halo $C_2$-$C_6$ alkynyl group; a $C_1$-$C_6$ alkoxy group; a halo $C_1$-$C_6$ alkoxy group; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; or a halo $C_1$-$C_6$ alkylsulfonyl group; and two groups of X residing in adjacent positions on the aromatic ring may be taken conjointly to form a fused ring, and said fused ring may have at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and l represents an integer of 0 to 2;

Y which may be the same or different represents a halogen atom; a $C_1$-$C_6$ alkyl group; a halo $C_1$-$C_6$ alkyl group; a cyclo $C_3$-$C_6$ alkyl group; a $C_1$-$C_6$ alkoxy group; a halo $C_1$-$C_6$ alkoxy group; a mono $C_1$-$C_6$ alkylamino group; a di $C_1$-$C_6$ alkylamino group which the $C_1$-$C_6$ alkyl groups may be the same or different; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenyl $C_1$-$C_4$ alkyl group; a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenoxy group; a substituted phenoxy group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenylthio group; a substituted phenylthio group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group; or a substituted heterocyclic group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and two groups of Y residing in adjacent positions on the aromatic ring may be taken conjointly to form a fused ring, and said fused ring may have at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and Y may be taken conjointly with $R^3$ to form a 5- to 7-membered ring which may be intercepted by one or two, the same or different oxygen atoms, sulfur atoms or nitrogen atoms; and m represents an integer of 0 to 3}.

2. A compound according to claim 1, wherein Z represents formula (II):

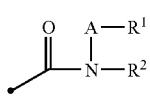
(II)

(wherein A, $R^1$ and $R^2$ are as defined below), or formula (III):

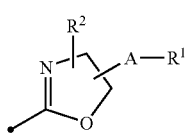
(III)

(wherein A represents a $C_1$-$C_6$ alkylene group; a substituted $C_1$-$C_6$ alkylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; a $C_2$-$C_6$ alkenylene group; a substituted $C_2$-$C_6$ alkenylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; a $C_2$-$C_6$ alkynylene group; or a substituted $C_3$-$C_6$ alkynylene group having at least one, the same or different substituents selected from the group consisting of halogen atom, cyano group, nitro group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group, $C_1$-$C_6$ alkylthio $C_1$-$C_6$ alkyl group, $C_1$-$C_6$ alkoxycarbonyl group and phenyl group; and an arbitrarily selected saturated carbon atom in the $C_1$-$C_6$ alkylene group, substituted $C_1$-$C_6$ alkylene group, $C_3$-$C_6$ alkenylene group, substituted $C_3$-$C_6$ alkenylene group, $C_3$-$C_6$ alkynylene group or substituted $C_3$-$C_6$ alkynylene group may be substituted with a $C_2$-$C_5$ alkylene group to form a $C_3$-$C_6$ cycloalkane ring; and arbitrarily selected two carbon atoms in the $C_2$-$C_6$ alkylene group, substituted $C_2$-$C_6$ alkylene group, $C_3$-$C_6$ alkenylene group and substituted $C_3$-$C_6$ alkenylene group may be taken conjointly together with an alkylene group or an alkenylene group to form a $C_3$-$C_6$ cycloalkane ring or a $C_3$-$C_6$ cycloalkene ring;

$R^1$ represents a hydrogen atom; a halogen atom; a cyano group; a nitro group, a $C_3$-$C_6$ cycloalkyl group; a $C_1$-$C_6$ alkoxycarbonyl group; a mono $C_1$-$C_6$ alkylaminocarbonyl group; a di $C_1$-$C_6$ alkylaminocarbonyl group which the $C_1$-$C_6$ alkyl groups may be the same or different; a mono $C_1$-$C_6$ alkylaminosulfonyl group; a di $C_1$-$C_6$ alkylaminosulfonyl group which the $C_1$-$C_6$ alkyl groups may be the same or different; a di $C_1$-$C_6$ alkoxyphosphoryl group which the $C_1$-$C_6$ alkyl groups may be the same or different; a di $C_1$-$C_6$ alkoxythiophosphoryl group which the $C_1$-$C_6$ alkyl groups may be the same or different; —C($R^5$)=NOR$^6$ (in this formula, $R^5$ represents a hydrogen atom or a $C_1$-$C_6$ alkyl group; and $R^6$ represents a hydrogen atom; a $C_1$-$C_6$ alkyl group; a $C_3$-$C_6$ alkenyl group; a $C_3$-$C_6$ alkynyl group; a $C_3$-$C_6$ cycloalkyl group; a phenyl $C_1$-$C_4$ alkyl group; or a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group and $C_1$-$C_6$ alkylthio group); a phenyl group; a substituted phenyl group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group; a substituted heterocyclic group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^1$-$R^7$ (in this formula, $A^1$ represents —O—, —S—, —SO—, —SO$_2$— or —N($R^6$)— (in this formula, $R^6$ is as defined above); and $R^7$ represents a hydrogen atom; a $C_1$-$C_6$ alkyl group; a halo $C_1$-$C_6$ alkyl group; a $C_3$-$C_6$ alkenyl group; a halo $C_3$-$C_6$ alkenyl group; a $C_3$-$C_6$ alkynyl group; a halo $C_3$-$C_6$ alkynyl group; a $C_3$-$C_6$ cycloalkyl group; a phenyl group; a substituted phenyl group having at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a phenyl $C_1$-$C_4$ alkyl group; a substituted phenyl $C_1$-$C_4$ alkyl group having, on the ring thereof, at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a heterocyclic group; a substituted heterocyclic group having, on the ring thereof, at least one, the same or different substituents selected from the group consisting of halogen atom, cyano group, nitro group, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a $C_1$-$C_6$ alkylcarbonyl group; a halo $C_1$-$C_6$ alkylcarbonyl group; a $C_1$-$C_6$ alokoxycarbonyl group; a mono $C_1$-$C_6$ alkylaminocarbonyl group; a di $C_1$-$C_6$ alkylaminocarbonyl group which the $C_1$-$C_6$ alkyl groups may be the same or different; a $C_1$-$C_6$ alkylsulfonyl group; a halo $C_1$-$C_6$ alkylsulfonyl group; a mono $C_1$-$C_6$ alkylaminosulfonyl group; a di $C_1$-$C_6$ alkylaminosulfonyl group which the $C_1$-$C_6$ alkyl groups may be the same or different; a di $C_1$-$C_6$ alkoxyphosphoryl group which the $C_1$-$C_6$ alkyl groups may be the same or different; or a di $C_1$-$C_6$ alkoxythiophosphoryl group which the $C_1$-$C_6$ alkyl groups may be the same or different);

$R^2$ represents a hydrogen atom; a $C_1$-$C_4$ alkyl group; a $C_1$-$C_4$ alkoxy $C_1$-$C_4$ alkyl group; or a $C_1$-$C_4$ alkylthio $C_1$-$C_4$ alkyl group; and $R^2$ may be taken conjointly together with A or $R^1$ to form one to three, the same or different, 5- to 7-membered rings which may be intercepted by oxygen atom, sulfur atom or nitrogen atom);

$R^3$ represents a hydrogen atom or a $C_1$-$C_4$ alkyl group; $R^4$ represents a a fluoro $C_1$-$C_6$ alkyl group; Rf represents a fluoro $C_1$-$C_6$ alkyl group; and X which may be the same or different represents a halogen atom; a nitro group; a cyano group; a $C_1$-$C_6$ alkyl group; a halo $C_1$-$C_6$ alkyl group; a $C_2$-$C_6$ alkenyl group; a halo $C_2$-$C_6$ alkenyl group; a $C_2$-$C_6$ alkynyl group; a halo $C_2$-$C_6$ alkynyl group; a $C_1$-$C_6$ alkoxy group; a halo $C_1$-$C_6$ alkoxy group; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; or a halo $C_1$-$C_6$ alkylsulfonyl group; l represents an integer of 0 to 2;

Y which may be the same or different represents a halogen atom; a $C_1$-$C_6$ alkyl group; a $C_1$-$C_6$ alkoxy group; a mono $C_1$-$C_6$ alkylamino group; a di $C_1$-$C_6$ alkylamino group which the $C_1$-$C_6$ alkyl groups may be the same or different; a $C_1$-$C_6$ alkylthio group; a $C_1$-$C_6$ alkylsulfinyl group; a $C_1$-$C_6$ alkylsulfonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenyl $C_1$-$C_4$ alkyl group; a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenoxy group; or a substituted phenoxy group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and m represents an integer of 0 to 2.

3. A compound according to claim 2, wherein Z represents formula (II):

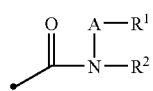

(II)

(wherein A, $R^1$ and $R^2$ are as defined below), or formula (III):

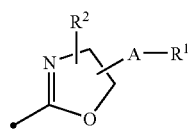

(III)

(wherein A represents an $C_1$-$C_6$ alkylene group;

$R^1$ represents a hydrogen atom; a halogen atom; a $C_1$-$C_6$ alkoxycarbonyl group; a mono $C_1$-$C_6$ alkylaminocarbonyl group; a di $C_1$-$C_6$ alkylaminocarbonyl group which the $C_1$-$C_6$ alkyl groups may be the same or different; a mono $C_1$-$C_6$ alkylaminosulfonyl group; a di $C_1$-$C_6$ alkylaminosulfonyl group which the $C_1$-$C_6$ alkyl groups may be the same or different; —C($R^5$)=$NOR^6$ (in this formula, $R^5$ represents a hydrogen atom or a $C_1$-$C_6$ alkyl group, and $R^6$ represents a hydrogen atom, a $C_1$-$C_6$ alkyl group, a $C_3$-$C_6$ alkenyl group or a $C_3$-$C_6$ alkynyl group); a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a heterocyclic group; a substituted heterocyclic group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; or -$A^1$-$R^7$ (in this formula, $A^1$ represents —O—, —S—, —SO—, —$SO_2$— or —N($R^6$)— (in this formula, $R^6$ is as defined above); and $R^7$ represents a hydrogen atom; a $C_1$-$C_6$ alkyl group; a halo $C_1$-$C_6$ alkyl group; a $C_3$-$C_6$ alkenyl group; a halo $C_3$-$C_6$ alkenyl group; a $C_3$-$C_6$ alkynyl group; a halo $C_3$-$C_6$ alkynyl group; a $C_3$-$C_6$ cycloalkyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a heterocyclic group; a substituted heterocyclic group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group, halo $C_1$-$C_6$ alkylsulfonyl group and $C_1$-$C_6$ alkoxycarbonyl group; a $C_1$-$C_6$ alkylcarbonyl group; a halo $C_1$-$C_6$ alkylcarbonyl group; a $C_1$-$C_6$ alkoxycarbonyl group; a mono $C_1$-$C_6$ alkylaminocarbonyl group; a di $C_1$-$C_6$ alkylaminocarbonyl group which the $C_1$-$C_6$ alkyl groups may be the same or different; a $C_1$-$C_6$ alkylsulfonyl group; a halo $C_1$-$C_6$ alkylsulfonyl group; a mono $C_1$-$C_6$ alkylaminosulfonyl group; a di $C_1$-$C_6$ alkylaminosulfonyl group which the $C_1$-$C_6$ alkyl groups may be the same or different; a di $C_1$-$C_6$ alkoxyphosphoryl group which the $C_1$-$C_6$ alkyl groups may be the same or different; or a di $C_1$-$C_6$ alkoxythiophosphoryl group which the $C_1$-$C_6$ alkyl groups may be the same or different); and $R^2$ represents a hydrogen atom or a $C_1$-$C_4$ alkyl group); and $R^3$ represents a hydrogen atom or a $C_1$-$C_4$ alkyl group; $R^4$ represents a fluoro $C_1$-$C_6$ alkyl group; Rf represents a fluoro $C_1$-$C_6$ alkyl group;

X which may be the same or different represents a halogen atom; a nitro group; a halo $C_1$-$C_6$ alkyl group; a halo $C_1$-$C_6$ alkoxy group; a halo $C_1$-$C_6$ alkylthio group; a halo $C_1$-$C_6$ alkylsulfinyl group; or a halo $C_1$-$C_6$ alkylsulfonyl group; and l represents an integer of 0 to 2;

Y which may be the same or different represents a halogen atom; a $C_1$-$C_6$ alkyl group; a $C_1$-$C_6$ alkoxy group; a mono $C_1$-$C_6$ alkylamino group; a di $C_1$-$C_6$ alkylamino group which the $C_1$-$C_6$ alkyl groups may be the same or different; a $C_1$-$C_6$ alkylthio group; a $C_1$-$C_6$ alkylsulfinyl group; a $C_1$-$C_6$ alkylsulfonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenyl $C_1$-$C_4$ alkyl group; a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenoxy group; or a substituted phenoxy group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, halo $C_1$-$C_6$ alkylsulfonyl group, $C_1$-$C_6$ alkylsulfonyl group and halo $C_1$-$C_6$ alkylsulfonyl group; and m represents an integer of 0 to 2.

4. A compound represented by formula (IV):

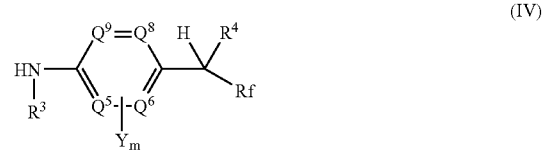

(IV)

(wherein $R^3$ represents a hydrogen atom; a $C_1$-$C_4$ alkyl group; a $C_1$-$C_4$ alkoxy $C_1$-$C_4$ alkyl group; or a $C_1$-$C_4$ alkylthio $C_1$-$C_4$ alkyl group; $R^4$ represents a fluoro $C_1$-$C_6$ alkyl group; and Rf represents a fluoro $C_1$-$C_6$ alkyl group;

$Q^5$, $Q^6$, $Q^8$ and $Q^9$ represent a carbon atom;

Y which may be the same or different represents a halogen atom; a $C_1$-$C_6$ alkyl group; a halo $C_1$-$C_6$ alkyl group; a $C_1$-$C_6$ alkoxy group; a halo $C_1$-$C_6$ alkoxy group; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenyl $C_1$-$C_4$ alkyl group; a substituted phenyl $C_1$-$C_4$ alkyl group having, on the ring thereof, at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenoxy group; or a substituted phenoxy group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and two groups of Y residing in the adjacent positions on the aromatic ring may be taken conjointly to form a fused ring, and said fused ring may have at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and m represents an integer of 0 to 3.

5. A compound according to claim 4, wherein $R^3$ represents a hydrogen atom or a $C_1$-$C_4$ alkyl group; $R^4$ represents a fluoro $C_1$-$C_6$ alkyl group; Rf represents a fluoro $C_1$-$C_6$ alkyl group; Y which may be the same or different represents a halogen atom; a $C_1$-$C_6$ alkyl group; a halo $C_1$-$C_6$ alkyl group; a $C_1$-$C_6$ alkoxy group; a halo $C_1$-$C_6$ alkoxy group; a $C_1$-$C_6$ alkylthio group; a halo $C_1$-$C_6$ alkylthio group; a $C_1$-$C_6$ alkylsulfinyl group; a halo $C_1$-$C_6$ alkylsulfinyl group; a $C_1$-$C_6$ alkylsulfonyl group; a halo $C_1$-$C_6$ alkylsulfonyl group; a phenyl group; a substituted phenyl group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; a phenoxy group; or a substituted phenoxy group having at least one, the same or different substituents selected from the group consisting of halogen atom, $C_1$-$C_6$ alkyl group, halo $C_1$-$C_6$ alkyl group, $C_1$-$C_6$ alkoxy group, halo $C_1$-$C_6$ alkoxy group, $C_1$-$C_6$ alkylthio group, halo $C_1$-$C_6$ alkylthio group, $C_1$-$C_6$ alkylsulfinyl group, halo $C_1$-$C_6$ alkylsulfinyl group, $C_1$-$C_6$ alkylsulfonyl group and halo $C_1$-$C_6$ alkylsulfonyl group; and m represents an integer of 0 to 3.

6. A compound according to claim 1, wherein Z represents formula (II):

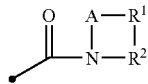

wherein A, $R^1$ and $R^2$ are defined according to claim 1.

7. A compound according to claim 2, wherein Z represents formula (II):

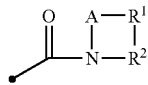

wherein A, $R^1$ and $R^2$ are defined according to claim 2.

8. A compound according to claim 3, wherein Z represents formula (II):

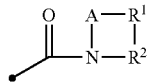

wherein A, $R^1$ and $R^2$ are defined according to claim 3.

9. A compound according to claim 1, wherein Z represents formula (III):

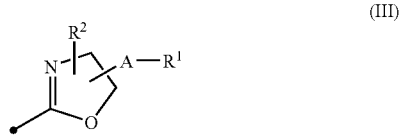

wherein A, $R^1$ and $R^2$ are defined according to claim 1.

10. A compound according to claim 2, wherein Z represents formula (III):

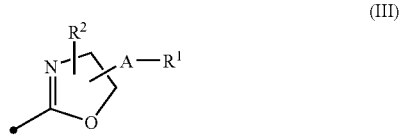

wherein A, $R^1$ and $R^2$ are defined according to claim 2.

11. A compound according to claim 3, wherein Z represents formula (III):

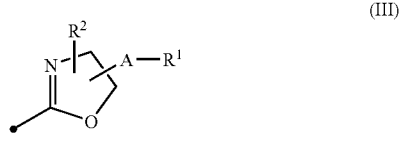

wherein A, $R^1$ and $R^2$ are defined according to claim 3.

12. An agrohorticultural insecticide comprising a compound according to claim 1 as an active ingredient and an agriculturally acceptable carrier.

13. A method of protecting plants from insects comprising applying an insecticidally effective quantity of an agrohorticultural insecticide according to claim 12, to a crop plant or a soil.

* * * * *